(12) United States Patent
Lee et al.

(10) Patent No.: US 8,445,268 B2
(45) Date of Patent: May 21, 2013

(54) HER-2/NEU DNA VACCINE HAVING ANTI-CANCER ACTIVITY

(75) Inventors: Joon Youb Lee, Seoul (KR);
Dong-Hyeon Kim, Seoul (KR);
Yeonseok Chung, Seoul (KR);
Sun-Young Chang, Seoul (KR);
Kyung-Chul Lee, Seoul (KR);
Chang-Yuil Kang, Seoul (KR)

(73) Assignee: ViroMed Co., Ltd. (KR)

(*) Notice: Subject to any disclaimer, the term of this patent is extended or adjusted under 35 U.S.C. 154(b) by 619 days.

(21) Appl. No.: 12/705,516

(22) Filed: Feb. 12, 2010

(65) Prior Publication Data
US 2010/0210714 A1 Aug. 19, 2010

Related U.S. Application Data

(63) Continuation of application No. 10/521,313, filed as application No. PCT/KR03/01400 on Jul. 15, 2003, now abandoned.

(30) Foreign Application Priority Data

Jul. 16, 2002 (KR) .................. 10-2002-0041764
Jun. 12, 2003 (KR) .................. 10-2003-0038012

(51) Int. Cl.
*C12N 15/00* (2006.01)
*C07H 21/04* (2006.01)
*A61K 48/00* (2006.01)

(52) U.S. Cl.
USPC ........ 435/320.1; 435/455; 435/476; 536/23.5; 536/24.1; 514/44

(58) Field of Classification Search
USPC ......... 435/320.1, 455, 476; 514/44; 536/23.5, 536/24.1
See application file for complete search history.

(56) References Cited

U.S. PATENT DOCUMENTS 7,005,498 B1 2/2006 Steinaa et al.
2006/0074038 A1 4/2006 Lee et al.

FOREIGN PATENT DOCUMENTS

WO WO 01/00244 * 1/2001
WO WO 01/00244 A2 1/2001

OTHER PUBLICATIONS

Piechocki et al, J. Immunol. 167: 3367-3374, 2001.*
Chen et al, Cancer Res. 58:1965-1971, 1998.*
Lee et al, J. Virol. 72(10):8430-8436, 1998.*
Lee et al, Biochem. Biophys. Res. Comm. 272(1): 230-235, 2000.*
Akiyama, T. et al., "The Product of the Human c-*erb*B-2 Gene: A 185-Kilodalton Glycoprotein with Tyrosine Kinase Activity," *Science* 232: 1644-1646, American Association for the Advancement of Science, US (1986).

Amici, A. et al., "DNA vaccination with full-length or truncated Neu induced protective immunity against the development of spontaneous mammary tumors in HER-2/neu transgenic mice," *Gene Therapy* 7:703-706, MacMillan Publishers Ltd. (2000).
Bernhard, H. et al., "Vaccination against the HER-2/neu oncogenic protein," *Endocrine-Related Cancer 9*: 33-44, Society for Endocrinology, GB (2002).
Bhattacharya, R. et al., "Efficacy of vaccination with plasmid DNA encoding for HER2/*neu* or HER2/*neu*-EGFP fusion protein against prostate cancer in rats," *Int. Immunopharm.* 2(6): 783-796, Elsevier, UK (2002).
Bocchia, M. et al., "Antitumor vaccination: where we stand," *Haematologica 85*:1172-1206, Ferrata Storti Foundation, IT(2000).
Chang, S. et al., "Enhanced Efficacy of DNA Vaccination Against Her-2/neu Tumor Antigen by Genetic Adjuvants," *Int. J. Cancer 111*: 86-95, Wiley-Liss Inc., US (2004).
Chen, S. et al., "Induction of Antitumor Immunity with Combination of HER2/neu DNA Vaccine and Interleukin 2 Gene-modified Tumor Vaccine," *Clin. Cancer Res. 6*: 4381-4388, American Association for Cancer Research, US (2000).
Chen, Y. et al., "DNA Vaccines Encoding Full-Length or Truncated Neu Induce Protective Immunity against Neu-expressing Mammary Tumors," *Cancer Res. 58*: 1965-1971, American Association for Cancer Research, US (1998).
Coussens, L. et al., "Tyrosine Kinase Receptor with Extensive Homology to EGF Receptor Shares Chromosomal Location with *neu* Oncogene," *Science 230*: 1132-1139, American Association for the Advancement of Science, US (1985).
Esserman, L. et al., "Vaccination with the extracellular domain of p185$^{neu}$ prevents mammary tumor development in *neu* transgenic mice," *Cancer Immunol. Immunther. 47*:337-342, Springer-Verlag, DE (1999).
Ewer, M. et al., "Cardiotoxicity in Patients Receiving Trastuzumab (Herceptin): Primary Toxicity, Synergistic or Sequential Stress, or Surveillance Artifact?" *Seminars in Oncology 26*(4): 96-101, W.B. Saunders Company, US (1999).
Foy, T. et al., "Designing HER2 Vaccines," *Seminars in Oncology* 29(11): 53-61, Elsevier Science, US (2002).
Ko, H., et al., "A Combination of Chemoimmunotherapies Can Effiiently Break Self-Tolerance and Induce Antitumor Immunity in a Tolerogenic Murine Tumor Model," *Cancer Research* 67(15):7477-7486, American Association for Cancer Research, US (2007).
Kobayashi, H. et al., "Defining Promiscuous MHC Class II Helper T-Cell Epitopes for the HER2/*neu* Tumor Antigen," *Cancer Res. 60*: 5228-5236, American Association for Cancer Research, US (2000).

(Continued)

*Primary Examiner* — Kevin Hill
(74) *Attorney, Agent, or Firm* — Sterne, Kessler, Goldstein & Fox P.L.L.C.

(57) ABSTRACT

The present invention relates to human Her-2/neu expressing plasmid constructs having anti-cancer activity and a DNA vaccine comprising same for preventing and/or treating cancer. The Her-2/neu DNA vaccines of the present invention can be effectively used as a therapeutic vaccine in reducing metastasis after tumor surgery or as a prophylactic vaccine for people with genetic high risk.

16 Claims, 18 Drawing Sheets

OTHER PUBLICATIONS

Lee, J. et al., "Comparison of the antitumor efficacies of Her-2/neu DNA vaccines inducing contrasting IgG immunity but comparable CTL activity in mice," *Vaccine* 21(5-6): 521-531, Elsevier, UK (2003).

Lee, S. et al., "Optimal Induction of Hepatitis C Virus Envelope-Specific Immunity by Bicistronic Plasmid DNA Innoculation with the Granulocyte-Macrophage Colony-Stimulating Factor Gene," *J. Virol.* 72(10): 8430-8436, American Society for Microbiology, US (1998).

Lee, Y. et al., "Improved Expression of Vascular Endothelial Growth Factor by Naked DNA in Mouse Skeletal Muscles: Implication for Gene Therapy of Ischemic Diseases," *Biochem. Biophys. Res. Comm.* 272(1): 230-235, Academic Press, UK (2000).

Lin, C. et al., "Therapeutic HER2/Neu DNA Vaccine Inhibits Mouse Tumor Naturally Overexpressing Endogenous Neu," *Molecular Therapy* 10(2): 290-301, The American Society of Gene Therapy, US (2004).

Piechocki, M. et al., "Complementary Antitumor Immunity Induced by Plasmid DNA Encoding Secreted and Cytoplasmic Human ErbB-2," *J. Immunol.* 167: 3367-3374, The American Association of Immunologists, US (2001).

Pilon, S. et al., "Vaccination with Cytoplasmic ErbB-2 DNA Protects Mice from Mammary Tumor Growth Without Anti-ErbB-2 Antibody," *J. Immunol.* 167: 3201-3206, The American Association of Immunologists, US (2001).

Rovero, S. et al., "DNA vaccination against rat Her-2/Neu p185 more effectively inhibits carcinogenesis than transplantable carcinomas in transgenic BALB/c mice," *J. Immunol.* 165: 5133-5142, The American Association of Immunologists, US (2000).

Slamon, D. et al., "Human Breast Cancer: Correlation of Relapse and Survival With Amplification of the HER-2/neu Oncogene," *Science* 235: 177-182, American Association for the Advancement of Science, US (1987).

Smorlesi, A. et al., "Evaluation of different plasmid DNA delivery systems for immunization against HER2/neu in a transgenic murine model of mammary carcinoma," *Vaccine* 24:1766-1775, Elsevier, UK (2006).

Urbanelli, L. et al., "Targeted Gene Transduction of Mammalian Cells Expressing the HER2/neu Receptor by Filamentous Phage", *J. Mol. Biol.* 313(5): 965-976, Academic Press, UK (2001).

Wei, W. et al., "Protection Against Mammary Tumor Growth by Vaccination with Full-Length, Modified Human *ErbB-2* DNA", *Int. J. Cancer 81*: 748-754, John Wiley & Sons, US (1999).

Yamamoto, T. et al., "Similarity of protein encoded by the human *c-erb*-B-2 gene to epidermal growth factor receptor," *Nature 319*: 230-234, Nature Publishing Group, UK (1986).

NCBI Entrez, GenBank Accession No. AX060704, Erickson, S. and Schwall, R., Sequence 2 from Patient WO0100244, Jan. 22, 2001.

Search Result for SEQ ID No. 2 (AX060704) from Patent Appl No. WO/0100244, Publ. date Jan. 4, 2001.

Office Action mailed Apr. 6, 2007, in U.S. Appl. No. 10/521,313, Lee, J. et al., 371 filed Jan. 14, 2005.

Office Action mailed Aug. 21, 2007, in U.S. Appl. No. 10/521,313, Lee, J. et al., 371 filed Jan. 14, 2005.

Office Action mailed Apr. 22, 2008, in U.S. Appl. No. 10/521,313, Lee, J. et al., 371 filing date Jan. 14, 2005.

Office Action mailed Jan. 15, 2009, in U.S. Appl. No. 10/521,313, Lee, J. et al., 371 filing date Jan. 14, 2005.

* cited by examiner

HER-2/NEU DNA VACCINE HAVING ANTI-CANCER ACTIVITY

CROSS REFERENCE TO RELATED APPLICATIONS

This application is a continuation of U.S. application Ser. No. 10/521,313, §371(c) Date Jan. 14, 2005, which is a U.S. National Phase application of International Application No. PCT/KR2003/001400, filed Jul. 15, 2003, which claims priority to KR 10-2003-0038012, filed Jun. 12, 2003 and KR 2002-0041764, filed Jul. 16, 2002, each of which are herein incorporated by reference in their entirety.

REFERENCE TO A SEQUENCE LISTING SUBMITTED ELECTRONICALLY VIA EFS-WEB

This application includes a sequence listing (name: "Substitute_Sequence Listing_ascii.txt"; size: 23,123 bytes; created on Apr. 28, 2010) submitted electronically via EFS-Web, which is incorporated herein by reference in its entirety.

FIELD OF THE INVENTION

The present invention relates to human Her-2/neu expressing plasmid constructs having anti-cancer activity and a DNA vaccine comprising same for preventing and treating cancer.

BACKGROUND OF THE INVENTION

The Her-2/neu or erbB-2 gene encodes a transmembrane protein that is a member of the type I family of growth factor receptors (Akiyama, T. et al., *Science* 232: 1644-1646, 1986). Amplification of this gene results in overexpression of the encoded 185 kDa receptor tyrosine kinase.

The Her-2/neu protein has been found to be amplified and overexpressed in several types of human adenocarcinomas, especially in tumors of the breast and the ovary. The overexpression was correlated with short relapse time and poor survival rate of breast cancer patients (Slamon, D. J. et al., *Science* 235: 177-182, 1987), suggesting that Her-2/neu overexpression likely plays a critical role in the development of human cancers. Several lines of evidence also support a direct role of Her-2/neu in the pathogenesis and clinical aggressiveness of Her-2/neu-expressing tumors (Kobayashi H. et al., *Cancer Res.* 60: 5228-5236, 2000). For example, Herceptin, a humanized anti-Her-2/neu monoclonal antibody used for treatment of Her-2/neu-expressing tumors, has been demonstrated to bring clinical benefits in advanced breast cancer patients (Ewer, M. S. et. al., *Semin. Oncol.* 26: 96, 1999). In addition, Her-2/neu-specific antibodies and T cells are detected in breast and ovarian cancer patients. Therefore, Her-2/neu oncogene is an excellent target for the development of therapeutic vaccines specific for Her-2/neu-overexpressing human cancers.

Since human Her-2/neu gene has tyrosine kinas activity in the intracellular domain and its overexpression itself stimulates abnormal cell division, there are several attempts to eliminate possible oncogenecity of Her-2/neu by introducing a mutation into the cytoplasmic kinase domain to inhibit tyrosine kinase activity or by constructing truncated Her-2/neu plasmids lacking the intracellular or extracellular domain (Wei, W. I. et al., *Int. J. Cancer* 81: 748-754, 1999)

Naked plasmids are attractive candidate vectors for the development of cancer vaccines encoding tumor-associated antigens. They are relatively simple to generate and safe to administer. Because they are not proteins nor associated with a viral coat, naked nucleic acids are not generally subject to neutralizing antibody reactions that can hamper the clinical efficacy of vaccines (Hellstrom, I. and Hellstrom, K. E., *J. Immunother.* 21: 119-126, 1998). In preclinical tumor models, DNA vaccines encoding rat (Chen, Y. et al., *Cancer Res.* 58: 1965-1971, 1998) or human Her-2/neu (Pilon, S. A. et al., *J. Immunol.* 167: 3201-3206, 2001) induced preventive efficacy against Her-2/neu expressing tumor cells.

Although successful preventive efficacy against Her-2/neu expressing tumor by DNA vaccination was achieved by many earlier experiments, no successful therapeutic efficacy was reported using only Her-2/neu expressing plasmids. The difficulty lies on the slow gain of antitumor immunity due to the lag time before antigenic expression of Her-2/neu expressing plasmids, while mammary tumor grows relatively fast. Therefore, some of the Her-2/neu therapeutic vaccine experiments were conducted based on the combination of DNA and cytokine-Secreting tumor cells (Chen, S. A. et al., *Clin. Cancer Res.* 6: 4381-4388, 2000), or dendritic cell (Chen, Y., *Gene Ther.* 8: 316-323, 2001).

Since a DNA vaccine has many advantages including mass-productivity, safety, and convenience (Gurunathan, S. et al., *Annu. Rev. Immunol.* 18:927-974, 2001), the present inventors have endeavored to develop Her-2/neu expressing plasmid constructs having high anti-cancer activity which can be effectively used as a DNA vaccine for preventing and treating cancer.

SUMMARY OF THE INVENTION

Accordingly, it is an object of the present invention to provide a human Her-2/neu expressing plasmid construct having high antitumor activity.

Another object of the present invention is to provide a DNA vaccine composition for preventing and/or treating cancer, comprising said plasmid construct and a pharmaceutically acceptable carrier.

An additional object of the present invention is to provide a method for preventing and/or treating cancer, comprising the step of administering an effective amount of said DNA vaccine.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

In accordance with one aspect of the present invention, there is provided Her-2/neu expressing plasmid constructs having anti-cancer activity which is prepared by inserting a truncated human Her-2/neu gene into pTV2 or pCK vector.

First, the present invention provides Her-2/neu expressing plasmid constructs encoding a truncated Her-2/neu gene that lacked the cytoplasmic kinase domain (intercellular domain), the truncated gene being selected because a plasmid encoding the full-length human Her-2/neu may adversely affect the physiology of the cells that takes up plasmid DNA. The truncated Her-2/neu gene has the nucleotide sequence of SEQ ID NO: 2 comprising the Her-2/neu transmembrane and extracellular domains, and is inserted into pTV2 vector which gives a high expression level of a foreign gene (Lee, S. W. et al., *J. Virol.* 72: 8430-8436, 1998)

The present invention also provides Her-2/neu expressing plasmid constructs encoding the truncated human Her-2/neu gene of SEQ ID NO: 3 that lacks the transmembrane domain of the Her-2/neu gene of SEQ ID NO: 2, which results in the secretion of the expressed protein into the cell exterior.

Further, the present invention provides Her-2/neu expressing plasmid constructs of which the signal peptide sequence is replaced by the herpes simplex virus type I glycoprotein D signal (gDs) sequence which is known to facilitate the efficient expression and secretion of human immunodeficiency virus type I gp160 (Berman, P. W. et al., *J. Virol.* 63: 3489-3498, 1989).

In a preferred embodiment of the present invention, four Her-2/neu expressing plasmid constructs based pTV2 vector (pNeu$_{TM}$, pNeu$_{ECD}$, pNeu$_{TM-gDs}$ and pNeu$_{ECD-gDs}$) are generated encoding either the Her-2/neu transmembrane and extracellular domains (pNeu$_{TM}$ and pNeu$_{TM-gDs}$) or only the Her-2/neu extracellular domain (pNeu$_{ECD}$ and pNeu$_{ECD-gDs}$), respectively (see A of FIG. 1). While pNeu$_{TM}$ or pNeu$_{ECD}$ encodes the original Her-2/neu signal peptide sequence, the signal peptide sequence of pNeu$_{TM-gDs}$ or pNeu$_{ECD-gDs}$ is replaced by the signal peptide sequence from glycoprotein D of herpes simplex virus type I.

Figure 2:
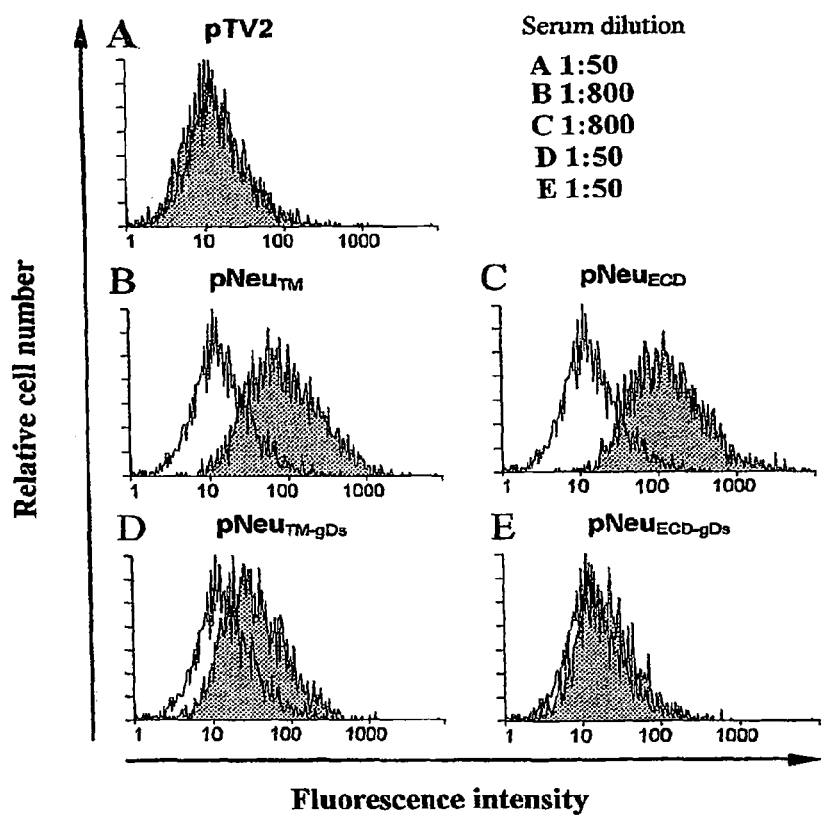
FIG. 2: representative FACS histograms of medium fluorescence intensity in each of the groups of mice vaccinated with pTV2 (A), pNeu$_{TM}$ (B), pNeu$_{ECD}$ (C), pNeu$_{TM\text{-}gDs}$ (D) and pNeu$_{ECD\text{-}gDs}$ (E), respectively;
  uncolored FACS histogram: control antibody,
  colored FACS histogram: anti-Her-2/neu antibody
Figure 3:
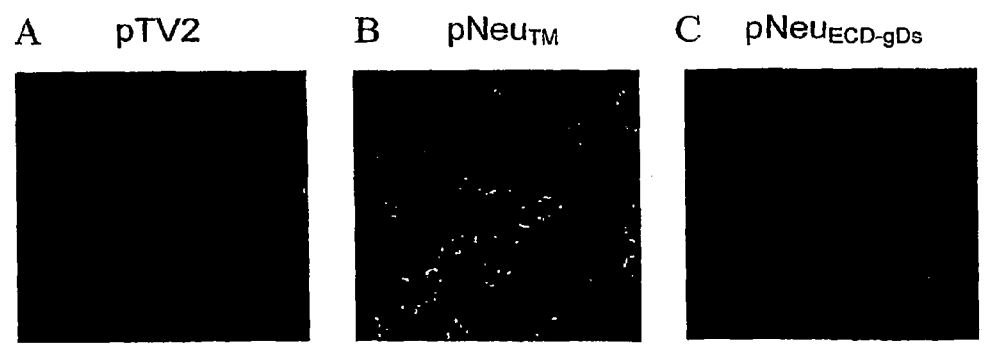
FIG. 3: confocal microscopic analysis of anti-Her-2/neu antibody in mouse sera immunized with pTV2 (A), pNeu (B) and pNeu$_{ECD\text{-}gDs}$ (C), respectively.
Figure 4:
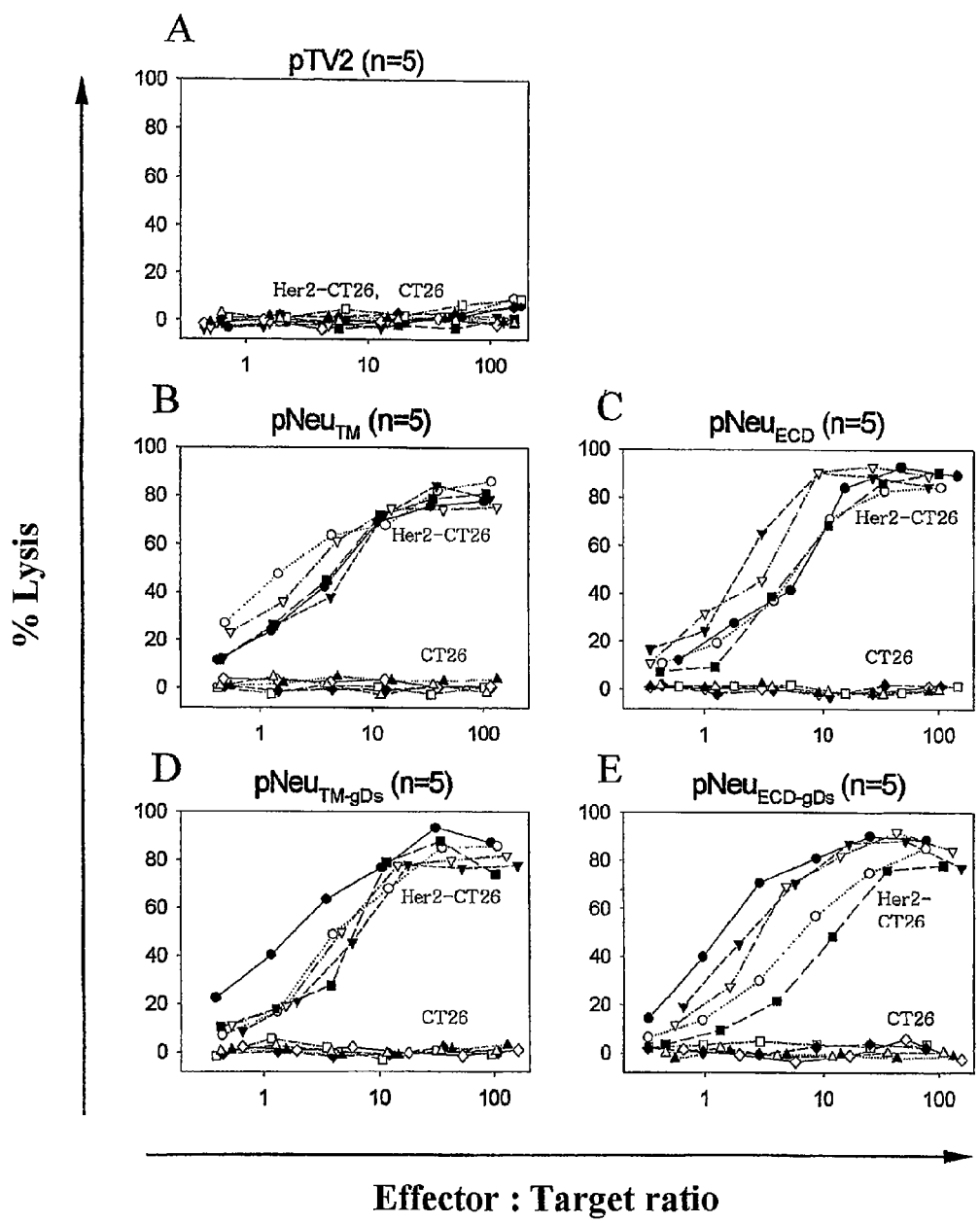
FIG. 4: $^{51}$Cr-release assays for comparing cytotoxic T lymphocytes (CTL) responses induced by vaccination with pTV2 (A), pNeu$_{TM}$ (B), pNeu$_{ECD}$ (C), pNeu$_{TM\text{-}gDs}$ (D) and pNeu$_{ECD\text{-}gDs}$ (E), respectively.

Whereas injections of pNeu$_{TM}$ or pNeu$_{ECD}$ encoding the original signal peptide sequence induce strong Her-2/neu-specific antibody response, pNeu$_{TM-gDs}$ or pNeu$_{ECD-gDs}$ encoding the signal sequence of herpes simplex virus type I glycoprotein D induce weak Her-2/neu-specific antibody response (see FIGS. 2 and 3). However, all pNeu constructs induce similar strong Her-2/neu-specific CTL response (see FIG. 4). These constructs can be used to evaluate whether a substantial difference in the quantity of Her-2/neu-specific antibody in mice could influence protective or therapeutic immunity against Her2-CT26, a syngeneic Her-2/neu-expressing tumor.

Figure 5:
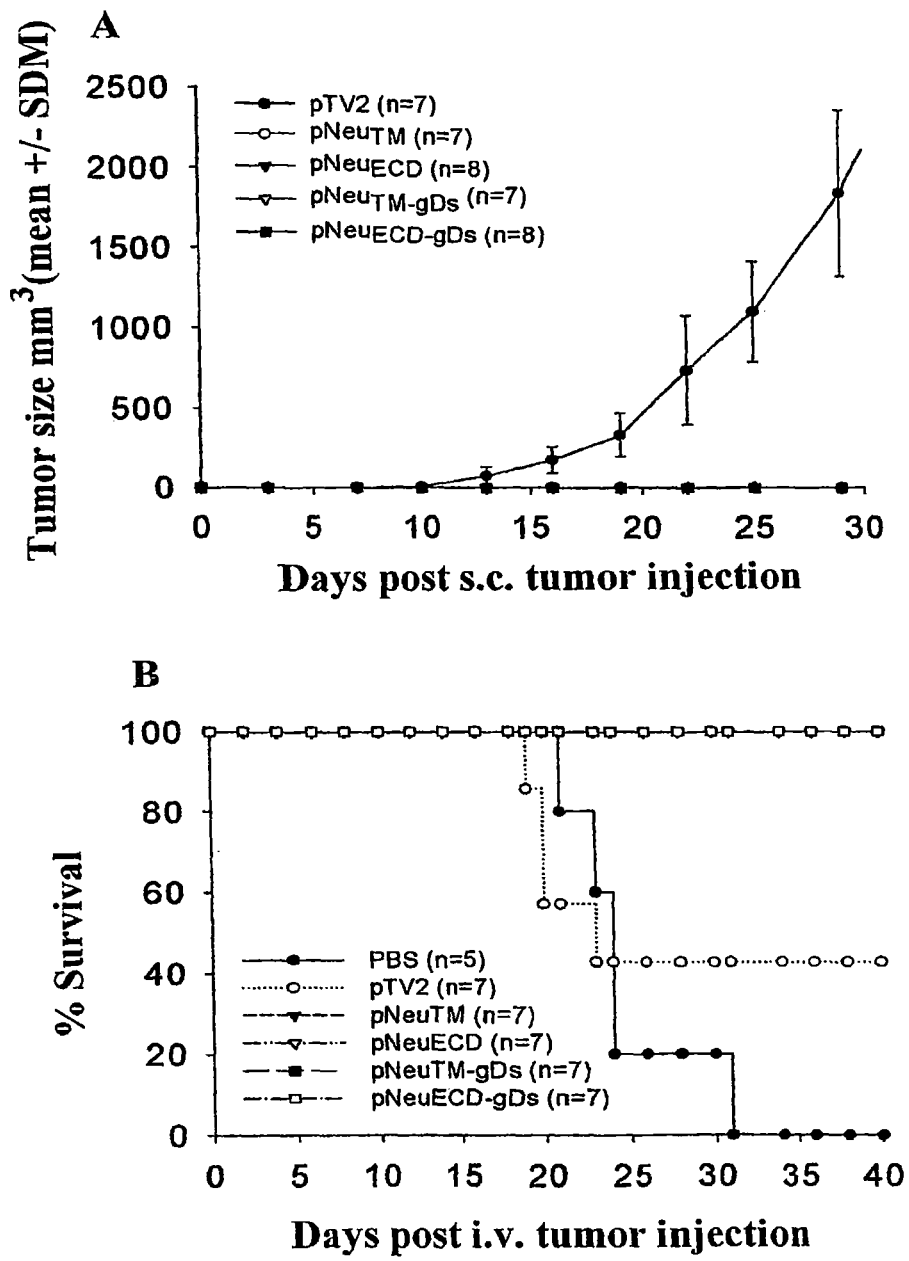
FIG. 5: preventive antitumor immunity induced by vaccination with pNeu constructs;
  A: tumor size in animal model subcutaneously injected with Her2-CT26 cells
  B: survival rate in animal model intravenously injected with Her2-CT26 cells

The present invention reveals that intramuscular (i.m.) injection of pNeu$_{TM}$, pNeu$_{ECD}$, pNeu$_{TM-gDs}$ or pNeu$_{ECD-gDs}$ can induce complete protection against a small number of Her2-CT26 cells (see FIG. 5). Moreover, preventive antitumor efficacies and pNeu$_{ECD-gDs}$ are not significantly different even when a maximum number of tumor cells are injected subcutaneous (s.c.) or intravenous (i.v.) (see FIG. 6). This suggests strong Her-2/neu CTL response without antibody response is as effective as the collaboration of strong CTL and antibody responses in a preventive model. However, when a large number of tumor cells are preinjected in a therapeutic model, only the mouse group having both strong CTL and antibody shows a significantly improved survival rate (see FIG. 7).

The Her-2/neu expressing plasmid constructs of the present invention have the advantage of eliminating possible oncogenecity of Her-2/neu by constructing truncated Her-2/neu plasmids lacking the Her-2/neu cytoplasmid kinase domain (intercellular domain). It therefore eliminates the risks of chance transforming of normal cells and transmission of abnormal growth signal toward tumor malignancy that may be caused by tyrosine kinase in the intracellular domain. In addition, the truncated Her-2/neu of the present invention enables to avoid the dangers of autoimmunity against the Her-2/neu intracellular domain that is highly conserved among the members of the EGFR (epidermal growth factor receptor) family. It has been reported that plasmid encoding the truncated Her-2/neu are at least as effective as a plasmid encoding the total Her-2/neu (Chen, Y. et al., *Cancer Res.* 58: 1965-1971, 1998). Also, the inventive Her-2/neu expressing plasmid constructs induce the both the Her-2/neu-specific antibody response and therapeutic antitumor effect.

These results demonstrate the relative roles of CTL and antibody by DNA vaccination in a preventive model or a therapeutic model against Her-2/neu-expressing tumor. Although strong CTL activation without antibody response by DNA vaccination could achieve enough preventive efficacy against Her-2/neu-expressing tumor challenge, DNA vaccines maximizing both arms of immune response was most beneficial in a therapeutic model.

To enhance the efficacy of the inventive vaccine in the clinical use, the present invention further provides Her-2/neu expressing plasmid constructs prepared by using a more efficient vector, pCK vector, in place of pTV2, to improve the expression level of Her-2/neu.

pCK vector has a stronger CMV promoter and smaller size (about 3 kb) than pTV2, and thus, a target antigen can be efficiently expressed at an increased concentration of pCK plasmid.

To prepare pCK plasmid constructs, the truncated Her-2/neu fragments from pNeu$_{TM}$ and pNeu$_{ECD}$, which have the original Her-2/neu signal peptide and strong antitumor activity, are each inserted into pCK vector.

In another preferred embodiment of the present invention, there are provided two Her-2/neu expressing plasmids based on pCK vector (pCK$_{TM}$ and pCK$_{ECD}$) which encode either the Her-2/neu transmembrane and extracellular domains (pCK$_{TM}$) or the Her-2/neu extracellular domain only (pCK$_{ECD}$).

Figure 8:
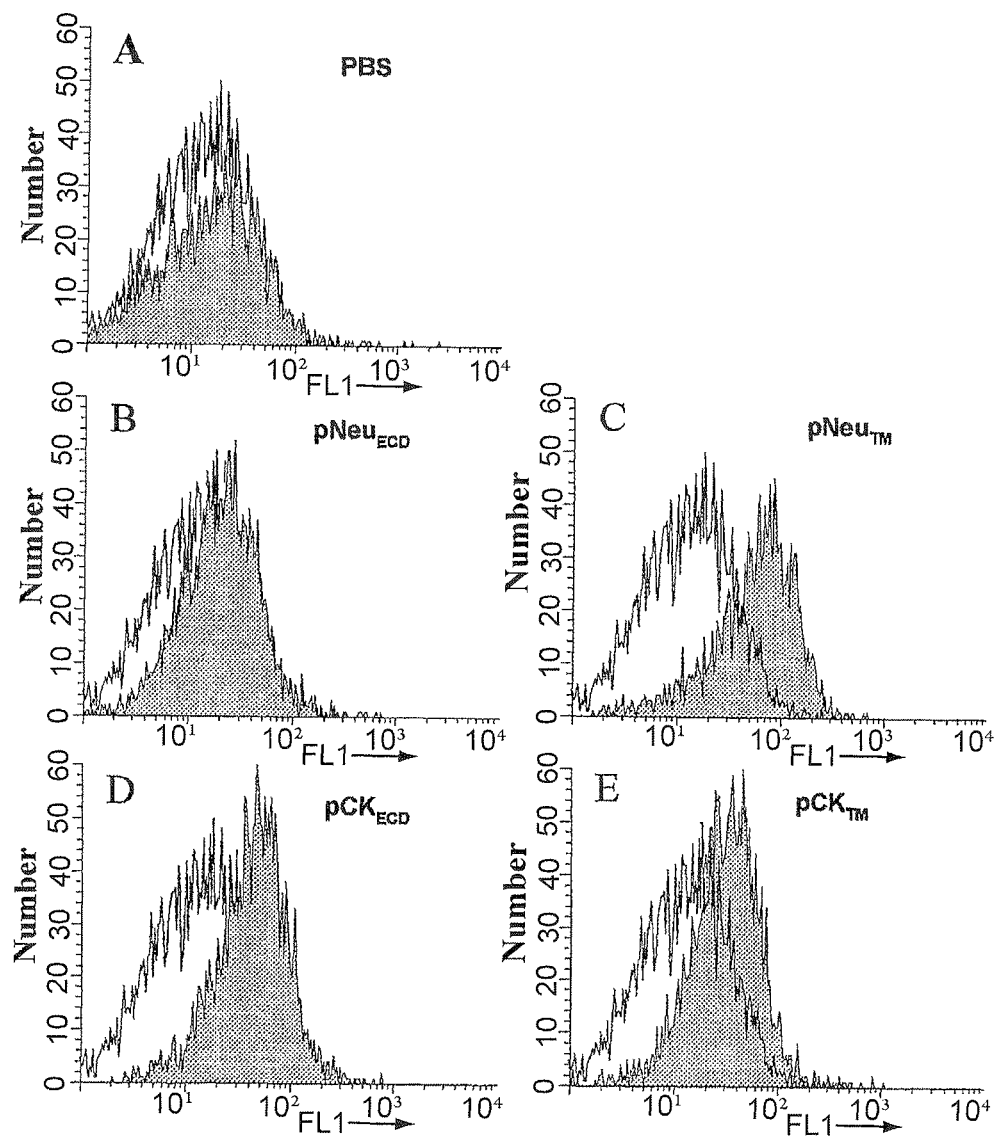
FIG. 8: representative FACS histograms of medium fluorescence intensity in each group of mice vaccinated with PBS (A), pNeu$_{ECD}$ (B), pNeu$_{TM}$ (C), pCK$_{ECD}$ (D) and pCK$_{TM}$ (E), respectively.
Figure 9:
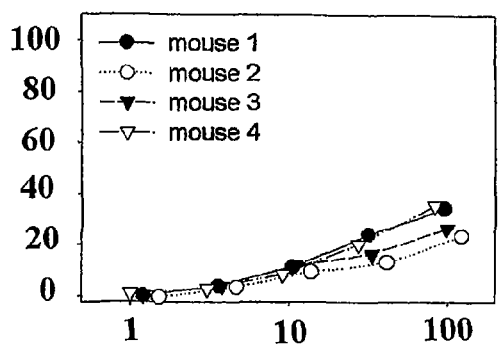
FIG. 9: $^{51}$Cr-release assays for comparing CTL responses induced by vaccination with PBS (A), pNeu$_{ECD}$ (B), pNeu$_{TM}$ (C), pCK$_{ECD}$ (D) and pCK$_{TM}$ (E), respectively.
Figure 9:
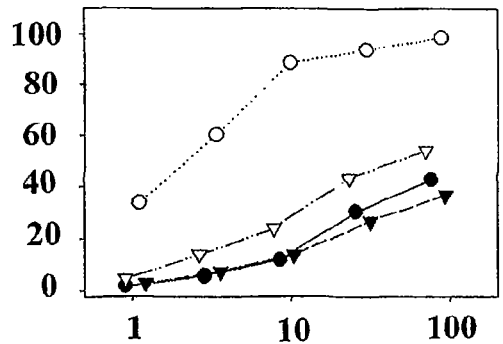
Figure 9:
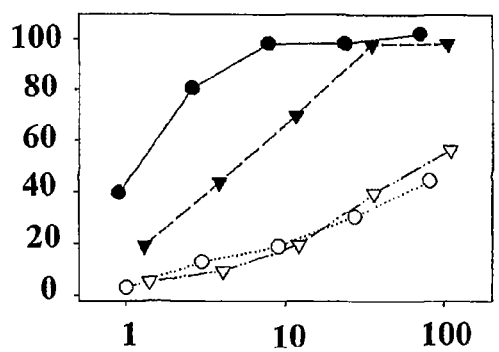
Figure 9:
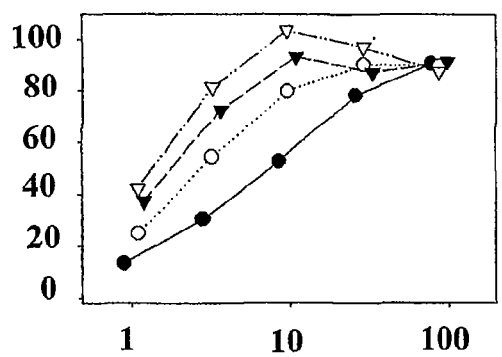
Figure 9:
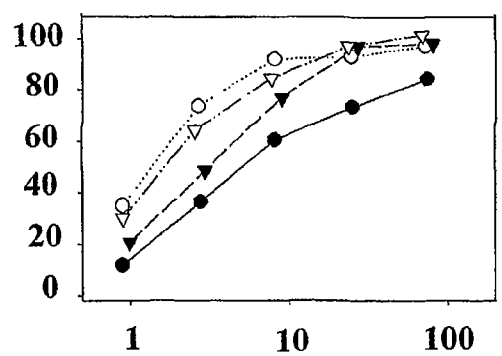

Vaccination with pCK$_{TM}$ and pCK$_{ECD}$ induce both strong antibody response and CTL response (see FIGS. 8 and 9). The extent of immunity induced by vaccination with pCK$_{TM}$ or pCK$_{ECD}$ is similar or slightly higher than observed for pNeu constructs. Intramuscular inoculation of pCK$_{TM}$ and pCK$_{ECD}$ completely prevent the growth of subcutaneous tumor and metastasis in a prevaccinated model and inhibit the tumor growth in a therapeutic model (see FIGS. 10 and 11).

Her-2/neu expressing plasmid constructs of the present invention, pNeu$_{TM}$, pNeu$_{ECD}$, pCK$_{TM}$ and pCK$_{ECD}$ have been deposited on Jun. 26, 2002 with the Korean Culture Center of Microorganisms (KCCM) (Address: #361-221, Yurim B/D, Hongje-1-dong, Seodaemun-gu, Seoul 120-091, Republic of Korea) under the accession numbers KCCM-10393, KCCM-10394, KCCM-103395 and KCCM-10396, respectively, in accordance with the terms of Budapest Treaty on the International Recognition of the Deposit of Microorganism for the Purpose of Patent Procedure.

Since pCK$_{TM}$ expressing truncated Her-2/neu is more efficient in inducing both humoral and cellular immunity, and the therapeutic antitumor activity of pCK$_{TM}$ is slightly better than that of pCK$_{ECD}$, pCK$_{TM}$ vaccination with in combination with cytokine genes is preferred.

Accordingly, the present invention discloses the use of a cytokine as an adjuvant which is helpful for overcoming immune tolerance against Her-2/neu in tumor patients.

Further in purpose, the present invention chose 6 cytokines; IL-12 (Alfonso, L. C. et al., *Science* 263: 235-237, 1994), IL-15 (Min, W. et al., *Vaccine* 20: 1466-1474, 2002), IL-18 (Hanlon, L. et al., *J. Virol.* 75: 8424-8433, 2001), Eta-1, Flt3L (Mwangi, W. et al., *J. Immunol.* 169: 3837-3846, 2002), GM-CSF (Lee, A. H. et al., *Vaccine* 17: 473-479, 1999). GM-CSF and Flt3L which induce the proliferation and activation of antigen presenting cells (APC) are expected to improve the delivery efficiency into APCs like dendritic cells and promote immune response including humoral and cellular immunity. IL-12, IL-15, IL-18 and Eta-1 are typical $T_H 1$ skewing cytokines and expected to induce cell-mediated immune responses important to cancer immunity.

Figure 12A:
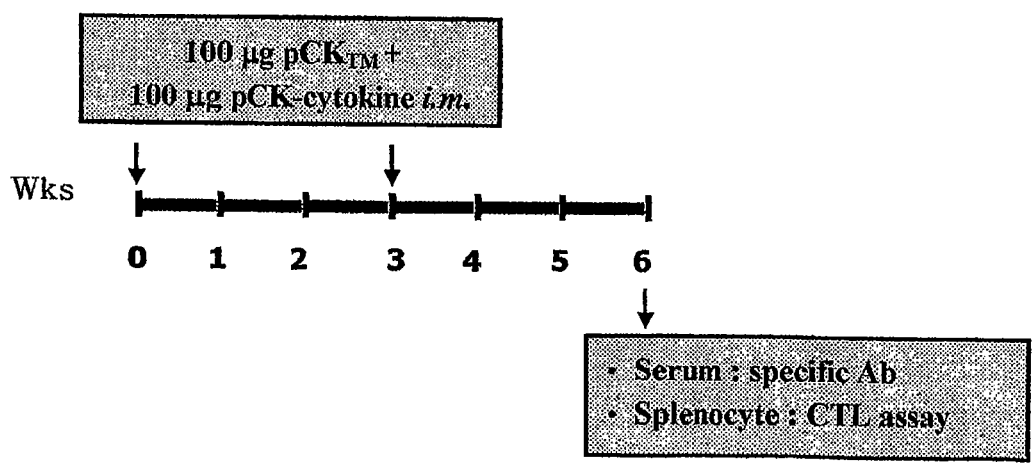
FIGS. 12a and 12b: vaccination schedule of co-injection with pCK$_{TM}$ and cytokine plasmids and $^{51}$Cr-release assays for comparing CTL responses induced thereby, respectively.

The present invention provides constructs pCK-IL12, pCK-IL15, pCK-IL18, pCK-Eta1, pCK-Flt3L and pCK-GMCSF which are obtained by inserting the respective cytokine gene into pCK vector. The effect of combining a cytokine gene adjuvant is similar to that observed for pCK$_{TM}$ in terms of antibody production and CTL response (see FIG. 12), but coinjection of pCK$_{TM}$ with each of the pCK-cytokines, especially pCK-GMCSF, enhances the antitumor effect in the preventive and therapeutic model (see FIGS. 13 and 14).

To enhance the cytokine adjuvant activity in the Her-2/neu DNA vaccination, the present invention constructed bicistronic plasmids, pCK$_{TM}$-GMCSF, pCK$_{TM}$-Flt3L, pCK$_{TM}$-Eta1, pCK$_{TM}$-IL12, pCK$_{TM}$-IL15, pCK$_{TM}$-IL18 and pCK$_{TM}$-IL23, in which the Her-2/neu protein and each of the cytokines are translated independently. Vaccinations with the inventive bicistronic plasmids also inhibit tumor growth and metastasis (see FIGS. 15 and 16). Antitumor activities of bicistronic plasmids except pCK$_{TM}$-IL18 are similar to those observed when two separate plasmids are coinjected. The antitumor activity of pCK$_{TM}$-IL18 is much higher than that of coinjection with pCK$_{TM}$ and pCK-IL18.

The above results show that the Her-2/neu expressing plasmid constructs of the present invention provide a vaccine that is not only preventive but also therapeutic against cancers. Therefore, Her-2/neu DNA vaccines have potential usage as a therapeutic vaccine in reducing metastasis after tumor surgery or as a prophylactic vaccine for people with genetic high risk.

In accordance with another aspect of the present invention, there is also provided Her-2/neu vaccine compositions used for preventing and treating cancer.

The inventive vaccine compositions include the human Her-2/neu expressing plasmid construct of the invention and a pharmaceutically acceptable carrier. These vaccine compositions can provide protection against (used as a prophylactic) infection by the antigen induced by the human Her-2/neu expressing plasmid construct of the invention. In addition, the vaccine compositions of the invention can be used to treat (used as a therapeutic) infection by the antigen induced by the human Her-2/neu expressing plasmid construct of the invention.

The preparation of vaccine compositions that contain the human Her-2/neu expressing plasmid construct of the invention as an effective ingredient is known to one skilled in the art. Typically, such vaccines are prepared as injectables, either as liquid solutions or suspensions; solid forms suitable for solution in, or suspension in, liquid prior to infection can also be prepared. The preparation can also be emulsified, or the protein encapsulated in liposomes. The active immunogenic ingredients are often mixed with carriers which are pharmaceutically acceptable and compatible with the active ingredient. The term "pharmaceutically acceptable carrier" refers to a carrier that does not cause an allergic reaction or other untoward effect in subjects to whom it is administered. Suitable pharmaceutically acceptable carriers include, for example, one or more of water, saline, phosphate buffered saline, dextrose, glycerol, ethanol, or the like and combinations thereof. In addition, if desired, the vaccine can contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. Other examples of adjuvants include DDA (dimethyldioctadecylammonium bromide), Freund's complete and incomplete adjuvants and QuilA. In addition, immune modulating substances such as lymphokines (e.g., IFN-g, IL-2 and IL-12) or synthetic IFN-g inducers such as poly I:C can be used in combination with adjuvants described herein.

Vaccine compositions of the present invention may be administered parenterally, by injection, for example, either subcutaneously or intramuscularly. Additional formulations which are suitable for other modes of administration include suppositories, and in some cases, oral formulations or formulations suitable for distribution as aerosols. In the case of the oral formulations, the manipulation of T-cell subsets employing adjuvants, antigen packaging, or the addition of individual cytokines to various formulation can result in improved oral vaccines with optimized immune responses. For suppositories, traditional binders and carriers may include, for example, polyalkylene glycols or triglycerides; such suppositories may be formed from mixtures containing the active ingredient in the range of 0.5 to 10%, preferably 1 to 2%. Oral formulations include such normally employed excipients as, for example, pharmaceutical grades of mannitol, lactose, starch magnesium stearate, sodium saccharine, cellulose, magnesium carbonate, and the like. These compositions take the form of solutions, suspensions, tablets, pills, capsules, sustained release formulations or powders and contain 10% to 95% of effective ingredient, preferably 25 to 70%.

The Her-2/neu expressing plasmid constructs of the present invention can be formulated into the vaccine compositions as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups can also be derived from inorganic bases such as, for example, sodium, potassium, ammonium, calcium, or ferric hydroides, and such organic bases as isopropylamine, trimethylamine, 2-ethylamino ethanol, histidine, procaine, and the like.

Vaccine compositions are administered in a manner compatible with the dosage formulation, and in such amount as will be prophylactically and/or therapeutically effective. The quantity to be administered depends on the subject to be treated, including, e.g., capacity of the subject's immune system to synthesize antibodies, and the degree of protection or treatment desired. Suitable dosage ranges are of the order of several hundred micrograms effective ingredient per vaccination with a range from about 0.01 to 10 mg/kg/day, preferably in the range from about 0.1 to 1 mg/kg/day. Suitable regiments for initial administration and booster shots are also variable but are typified by an initial administration followed by subsequent inoculations or other administrations. Precise amounts of effective ingredient required to be administered depend on the judgment of the practitioner and may be peculiar to each subject. It will be apparent to those of skill in the art that the therapeutically effective amount of Her-2/neu expressing plasmid constructs of this invention will depend, inter alia, upon the administration schedule, the unit dose of antigen administered, whether the Her-2/neu expressing plasmid construct is administered in combination with other therapeutic agents, the immune status and health of the recipient, and the therapeutic activity of the particular Her-2/neu expressing plasmid construct.

The compositions can be given in a single dose schedule, or preferably in a multiple dose schedule. A multiple dose schedule is one in which a primary course of vaccination can include 1 to 10 separate doses, followed by other doses given at subsequent time intervals required to maintain and or reinforce the immune response, for example, at 1 to 4 months for a second dose, and if needed, a subsequent dose(s) after several months. Periodic boosters at intervals of 1 to 5 years, usually 3 years, are desirable to maintain the desired levels of protective immunity.

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation.

In one aspect, an adjuvant effect is achieved by use of an agent such as alum used in about 0.05 to about 0.1% solution in phosphate buffered saline. Alternatively, the antigen is made as an admixture with synthetic polymers of sugars (Carbopol. R™) used as an about 0.25% solution. Adjuvant effect may also be made by aggregation of the antigen in the vaccine by heat treatment with temperatures ranging between about 70 to about 101° C. for a 30 sec to 2 min period, respectively. Aggregation by reactivating with pepsin treated (Fab) antibodies to albumin, mixture with bacterial cell(s) such as *C. parvum* or an endotoxin or a lipopolysaccharide components of Gram-negative bacteria, emulsion in physiologically acceptable oil vehicles such as mannide monooleate (Aracel A) or emulsion with a 20% solution of a perfluorocarbon (Fluosol-DA. R™) used as a block substitute also may be employed.

Various polysaccharide adjuvants may also be used. For example, the use of various pneumococcal polysaccharide adjuvants on the antibody responses of mice has been described. The doses that produce optimal responses, or that otherwise do not produce suppression, should be employed as indicated. Polyamine varieties of polysaccharides are particularly preferred, such as chitin and chitosan, including deacetylated chitin.

Another adjuvant contemplated for use in the present invention is BCG. BCG (Bacillus Calmette-Guerin, an attenuated strain of *Mycobacterium*) and BCG-cell wall skeleton (CWS) may also be used as adjuvants in the invention. BCG is an important clinical tool because of its immunostimulatory properties. BCG acts to stimulate the reticuloendothelial system, activates natural killer cells and increases proliferation of hematopoietic stem cells. Cell wall extracts of BCG have proven to have excellent immune adjuvant activity. In a typical practice of the present invention, cells of *Mycobacterium bovis* BCG are grown and harvested by methods known in the art. Besides *Mycobacterium bovis* BCG, vaccines of non-pathogenic bacteria, e.g., *Salmonella* sp., *Pseudomonas* sp., *Eschericia* sp., and so on can be used in the present invention.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

Reference Example 1

Cell Lines and Animals

The Her-2/neu expressing human breast carcinoma SK-BR3 cell line (ATCC HTB-30) and murine colon adenocarcinoma cell line CT26 (ATCC CRL-2639) were obtained from the American Type Culture Collection (Manassas, Va., USA). Human breast cancer cell line SK-BR3 cells were maintained in RPMI1640 (BioWhittaker, Walkersvile, Md.) supplemented with 10% heat-inactivated fetal bovine serum (FBS, GIBCO, Gaithersburg, Md.) and 1% penicillin-streptomycin (GIBCO). Her-2/neu-expressing transfectoma Her2-CT26 cells were prepared by transduction of CT26 cells with the cDNA-encoding human Her-2/neu (NCBI: M1730). Her2/CT26 and CT26 cells were cultured in IMDM (Bio-Whittaker) containing 10% heat-inactivated FBS and 1% penicillin-streptomycin.

Female 5-week-old BALB/C mice were purchased from Charles River (Osaka, Japan) and kept at 22° C., 55% relative humidity, and a daily lighting cycle of 12 hrs light/12 hrs dark with free access to food and water. The mice were housed at Laboratory Animal Center of Seoul National University until use and kept in a germ-free isolator (Techniplast, Buguggiate, Italy) during the whole experiments.

Reference Example 2

Isolation of DNA Plasmids for i.m. Injection

*Escherichia coli* strain DH5α, transformed with each of the plasmids, $pNeu_{TM}$, $pNeu_{ECD}$, $pNeu_{TM-gDs}$, $pNeU_{ECD-gDs}$ $pCK_{TM}$ and $pCK_{ECD}$, control vectors pTV2 and pCK, was grown in LB broth (Difco, Detroit, Mich.). Large-scale preparation of the plasmid DNA was carried out by the alkaline lysis method using an Endofree Qiagen Plasmid-Giga kit (Qiagen, Chatsworth, Calif.) according to the manufacturer's instructions. DNA was then precipitated, suspended in sterile PBS (BioWhittaker) at a concentration of 2 mg/ml, and stored in aliquots at −20° C. for subsequent use in immunization protocols.

Reference Example 3

Flow Cytometry (FACS)

To examine whether sera could specifically react Her-2/neu surface protein, SK-BR3, Her2-CT26 and CT26 cells were stripped from the culture flasks with a cell scraper (Nunc, Naperville, Ill.). Removed cells were washed in an FACS buffer consisting of RPMI1640 supplemented with 2% FBS and 0.1% sodium azide. Approximately $2 \times 10^5$ cells per analysis were incubated together with a serial dilute of a serum or control antibody at 4° C. for 30 min. Cells were washed 3 times a serial dilute of the same FACS buffer and then stained for 30 minutes at 4° C. with an FITC-conjugated goat monoclonal antibody specific for mouse IgG (Sigma). Stained cells were washed 2 times and resuspended in the same FACS buffer. To exclude dead cells from data, 1 μg/ml propidium iodide (Sigma) was added to the cell suspension and incubated for 30 sec prior to analysis. Only the cells that were negative by propidium iodide staining were gated and further analyzed for binding to tumor cells. Flow cytometry was performed using a PAS IIIi flow cytometer (Partec GmbH, Munster, Germany)

Reference Example 4

Confocal Microscopy for Anti-Her-2/neu Antibodies

Approximately $1 \times 10^4$ SK-BR3 cells were grown for three days on Lab-Tek chambered coverglass (Nunc, Naperville, Ill.) coated with 1 mg/ml poly-L-Lysine. Cells were fixed with 4% paraformaldehyde in PBS for 10 min at room temperature, washed three times with DMEM, blocked with 1% goat γ-globulin in DMEM for 1 hour at 4° C., incubated with 1:50 diluted mouse sera in a blocking solution for 8 hours at 4° C., washed, and incubated with R-phycoerythrin-conjugated goat anti-mouse immunoglobulin secondary antibody (Southern Biotech, Birmingham, Ala.) for 30 min at room temperature. Slides were then mounted on Gel/Mount media (Fisher) and examined using a confocal microscopy (Leica TCS-SP laser scanning microscopy).

Reference Example 5

DNA Immunization Method

Briefly, each mouse received an i.m. injection of 100 μg of plasmid DNA that was dissolved in 100 μl of sterile PBS into the anterior tibialis muscle. The inoculation site was pretreated with bupivacaine-HCl (ASTRA, Westborough, Mass.). For daily immunization for therapeutic vaccination, bupivacaine-HCl was pretreated only once just before the first immunization. Sera were collected via the retro-orbital plexus at selected time points and monitored for the presence of anti-Her-2/neu antibodies.

Reference Example 6

Chromium-Release Assays

Splenocytes prepared by extracting spleen from immunized mice were cultured with mytomycin-C treated Her2-CT26 cells for 6 days, and were assayed for the lysis of CT26 or Her2-CT26 target cells in a 4 hour $^{51}$Cr-release assay.

Her2-CT26 or CT26 tumor target cells were labeled with $^{51}$Cr by incubating $2 \times 10^6$ cells with 200 μCi Na$^{51}$CrO$_4$ (NEN Research Products, Boston, Mass.) in 200 μl saline at 37° C. for 90 min. The unincorporated $^{51}$Cr was removed by four washes with RPMI1640. Graded numbers of effector cells were mixed with 10000 labeled target cells in 200 μl RPMI plus 10% FBS in the wells of a round-bottom microtiter plate. The plate was incubated at 37° C. for 4 hours. After the incubation, the plate was centrifugated, and a 100 μl aliquot was removed from each well for counting with a γ-scintillation counter (Packard, Minaxi Auto Gamma 5000 Series). The percent lysis was calculated by formula 1:

$$\text{percent specific lysis } (\%) = 100 \times [(\text{cpm}_{experimental} - \text{cpm}_{spontaneous}) / (\text{cpm}_{max} - \text{cpm}_{spontaneous})] \quad \text{<Formula 1>}$$

The $\text{cpm}_{max}$ value was determined by adding 10 μl of 5% triton-X (Sigma) to wells containing $^{51}$Cr-labeled target cells. Each group contained a duplicate. The $\text{cpm}_{spontaneous}$ value was determined by adding only an equal volume of the medium without the addition of splenocytes or triton-X.

Reference Example 7

Tumor Challenge

Mice were challenged by injection with Her2-CT26 cells suspended in sterile PBS either subcutaneously on the flank or intravenously. The three-dimensional size of each tumors was measured with a caliper, and the volume was calculated by formula 2:

tumor volume (mm³)=(width×length×depth) mm³× π/6   <Formula 2>

Animals were monitored twice a week for the development of palpable tumors. Mice showing any symptom of acute sickness, hard to breathe or rare movement were sacrificed.

Example 1

Construction of Her-2/neu Expressing Plasmids pTV2 and pTV2-gDs (Lee, S. W. et al., *J. Virol.* 72:8430-8436, 1998) and pCK (Lee Y, et. al., *Biochem Biophys Res Commun.* 272:230-235, 2000; Deposit Accession No: KCCM-10179) were used an expression vectors. pTV2-gDs is an expression vector which was cloned to contain the signal sequence of herpes simplex virus type 1 glycoprotein D in expression vector pTV2. The cDNA encoding the entire human Her-2/neu gene (SEQ ID NO: 1) was inserted into the pRC/CMV backbone (Invitrogen, San Diego, Calif.) to produce a full-length Her-2/neu plasmid (9.6 Kb).

The plasmid pNeu$_{ECD}$, encoding the extracellular domain of Her-2/neu without the intracellular and transmembrane domains of Her-2/neu, was generated from the PCR product of the full-length Her-2/neu plasmid using NF6 (SEQ ID NO: 4) and NSR1 (SEQ ID NO: 5) as a primer pair, and cloned into the KpnI and XbaI sites of pTV2. Similarly, the plasmid pNeu$_{TM}$, encoding the extracellular and transmembrane domains of Her-2/neu, was generated from the PCR product of the full-length Her-2/neu plasmid using NF5 SEQ ID NO: 6) and NRM2 (SEQ ID NO: 7) as a primer pair, and cloned into the KpnI and XbaI sites of pTV2 (FIG. 1).

The plasmid pNeu$_{ECD\text{-}gDs}$, encoding the extracellular domain of Her-2/neu without the intracellular and transmembrane domains of Her-2/neu, was generated from the PCR product of the full-length Her-2/neu plasmid using NSF2 (SEQ ID NO: 8) and NSR1 (SEQ ID NO: 5) as a primer pair, and cloned into the AscI and XbaI sites of pTV2-gDs. Similarly, the plasmid pNeu$_{TM\text{-}gDs}$, encoding the extracellular and transmembrane domains of Her-2/neu, was generated from the PCR product of the full-length Her-2/neu plasmid using NF3 (SEQ ID NO: 9) and NRM2 (SEQ ID NO: 7) as a primer pair, and cloned into the AscI and XbaI sites of pTV2-gDs. The plasmids pCK$_{ECD}$ and pCK$_{TM}$ were prepared by inserting into the KpnI-XbaI site of pCK vector truncated Her-2/neu gene fragments obtained from pNeu$_{ECD}$ and pNeu$_{TM}$, respectively. PCR was carried out at 94° C. for 2 min; 94° C. for 15 sec, 55° C. for 30 sec and 68° C. for 3.5 min; and 72° C. for 7 min.

Figure 1A:
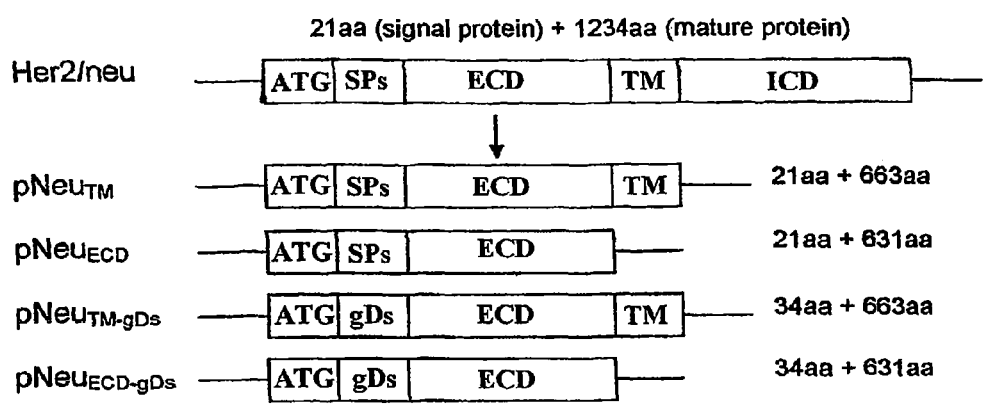
FIGS. 1a and 1b: schematic procedure for preparing recombinant human pNeu plasmid constructs and a preset immunization schedule, respectively;
  ECD: extracellular domain,
  TM: transmembrane domain,
  ICD: intracellular domain

Thus generated were four Her-2/neu expressing plasmids (pNeu$_{TM}$, pNeu$_{ECD}$, pNeu$_{TM\text{-}gDs}$, and pNeu$_{ECD\text{-}gDs}$), each encoding both the Her-2/neu transmembrane and extracellular domains (pNeu$_{TM}$ and pNeu$_{TM\text{-}gDs}$) or only the Her-2/neu extracellular domain (pNeu$_{ECD}$ and pNeu$_{ECD\text{-}gDs}$) (FIG. 1a). While pNeu$_{TM}$ or pNeu$_{ECD}$ encoded the original Her-2/neu signal peptide sequence, the signal peptide sequence of pNeu$_{TM\text{-}gDs}$ or pNen$_{ECD\text{-}gDs}$ was replaced by the signal peptide sequence from glycoprotein D of herpes simplex virus type I.

Example 2

Induction of Anti-Her-2/neu Antibody by pNeu Constructs Vaccination

Tests were conducted to examine whether various pNeu plasmid constructs could induce anti-Her-2/neu antibodies as follows.

Figure 1B:
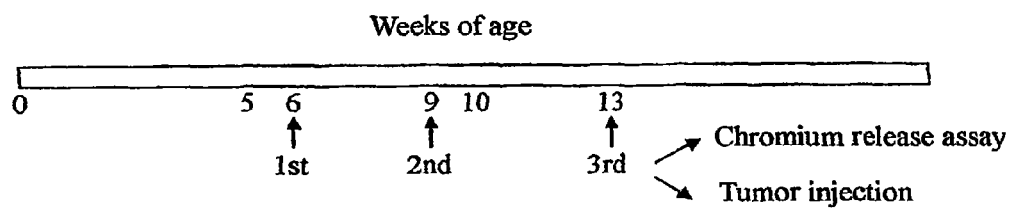

Each mouse prepared in Reference Example 1 received three i.m. injections of 100 µg of plasmid DNA prepared in Reference Example 2 according to a preset immunization schedule (FIG. 1b). Some mice of each group were sacrificed and the lytic function of Her-2/neu-specific CTL was determined. Other mice were challenged with Her-2/neu expressing tumor for evaluating antitumor immunity. Sera were obtained from BALB/c mice before the first injection and one week after the third vaccination, and the anti-Her-2/neu antibody titer in the serum was measured based on its binding to the breast cancer cell line, SK-BR3, using a flow cytometry. Her-2/neu-specific serum IgG titers of all mice vaccinated with pNeu$_{TM}$, pNeu$_{ECD}$, pNeu$_{TM\text{-}gDs}$, or pNeu$_{ECD\text{-}gDs}$ were determined and presented based on the greatest dilution of serum for which a shift in the mean fluorescence intensity of binding affinity to SK-BR3 cells was seen relative to an irrelevant control antibody.

TABLE 1

| pTV2 (n = 5) | pNeu$_{TM}$ (n = 5) | pNeu$_{ECD}$ (n = 5) | pNeu$_{TM\text{-}gDs}$ (n = 5) | pNeu$_{ECD\text{-}gDs}$ (n = 5) |
|---|---|---|---|---|
| <50 | 12800 | 12800 | 800 | <50 |
| <50 | 12800 | 12800 | 50 | <50 |
| <50 | 3200 | 12800 | <50 | <50 |
| <50 | 12800 | 12800 | 800 | <50 |
| <50 | 3200 | 12800 | 50 | <50 |

As shown in Table 1, the observed IgG titers were ranked in the order of pNeu$_{ECD}$>pNeu$_{TM}$>pNeu$_{TM\text{-}gDs}$>pNeu$_{ECD\text{-}gDs}$=pTV2. As expected, none of the sera collected from animals before the injection of plasmid DNA had detectable anti-Her-2/neu binding activities. Moreover, none of the animals injected with pTV2 made detectable anti-Her-2/neu antibodies at 1:50 dilution. However, vaccination with pNeu$_{TM}$ or pNeu$_{ECD}$ resulted in high Her-2/neu-specific IgG titers (FIG. 2, A) and serum samples diluted by 1:800 produced a wide shift in the mean fluorescence intensity (FIG. 2, B and C). In contrast, vaccination with pNeu$_{TM\text{-}gDs}$ or pNeu$_{ECD\text{-}gDs}$ resulted in a low or undetectable IgG titer and serum samples diluted by 1:50 revealed a little or a barely detectable shift in the mean fluorescence intensity (FIG. 2, D and E).

The existence of Her-2/neu-specific antibodies in mouse sera immunized with pNeu$_{TM}$ or pNeu$_{ECD\text{-}gDs}$ was also confirmed by confocal microscopic analysis. Mouse serum immunized with pNeu$_{TM}$ (FIG. 3, B) demonstrated clear localization of anti-Her-2/neu antibodies on the surface of SK-BR3 that was not shown with the mouse sera immunized with pTV2 (FIG. 3, A) or pNeu$_{ECD\text{-}gDs}$ (FIG. 3, C), which is consistent with the anti-Her-2/neu antibody titers presented in FIG. 2.

Example 3

Induction of Her-2/neu-Specific CTL by pNeu Constructs Vaccination

Having demonstrated that vaccination with pNeu constructs boosted high to very low Her-2/neu-specific antibody responses in vaccinated mice (FIG. 2), Her-2/neu-specific CTL responses induced in the same mice were evaluated as follows.

Splenocytes were prepared 2 weeks after the third immunization from the same mice that were tested for Her-2/neu-specific serum IgG titers. Splenocytes were cultured with mytomycin-C-treated human Her-2/neu expressing syngeneic murine transfectoma, Her2-CT26 cells for 6 days, and were assayed for the lysis of CT26 or Her2-CT26 target cells by a 4-h $^{51}$Cr-release assay.

As a result, splenocytes from mice vaccinated with pNeu$_{TM}$ (FIG. 4, B), pNeu$_{ECD}$ (FIG. 4, C), pNeu$_{TM\text{-}gDs}$ (FIG. 4, D), or pNeu$_{ECD\text{-}gDs}$ (FIG. 4, E) exhibited CTL-dependent lysis of Her2-CT26 that was not shown with splenocytes from pTV2 vaccinated control mice (FIG. 4, A) and the relative strength of Her-2/neu-specific CTL response was in order of pNeu$_{TM}$>pNeu$_{ECD}$>pNeu$_{TM\text{-}gDs}$>pNeu$_{ECD\text{-}gDs}$>pTV2. Percent Her-2/neu-specific lysis by splenocytes from mice immunized with any one of pNeu constructs was comparable to the others of pNeu constructs and were 80~90% at an E:T ratio of 50:1 and 60~70% at an E:T ratio of 10:1 (FIG. 3, B to E). However, splenocytes from any group of mice did not induce CTL-dependent lysis of CT26 cells.

In brief, all Her-2/neu expressing plasmids induced strong Her-2/neu-specific CTL response, which was irrelevant to their signal peptide sequences. However, they induced substantially different Her-2/neu-specific antibody responses according to their signal peptide sequences. Only pNeu$_{TM}$ and pNeu$_{ECD}$ with the original signal sequence showed high Her-2/neu-specific IgG titers (FIG. 2). When their signal sequence was replaced by a viral signal sequence, pNeu$_{TM\text{-}gDs}$ generated a low level of anti-Her-2/neu antibodies, and pNeu$_{ECD\text{-}gDs}$, a very low level of anti-Her-2/neu antibodies.

Example 4

Prevention of Tumor Growth by pNeu Constructs Vaccination

Antitumor immunity against human Her-2/neu expressing syngeneic murine tumor cell line Her2-CT26 in mice was evaluated as follows.

Initially, titration studies were performed to determine the optimal number of tumor cells to be injected s.c. or i.v. into mice to generate subcutaneous tumor formation or lung metastasis, and the results showed that Her2-CT26 cells induced subcutaneous or lung metastatic tumor in BALB/c mice when 5×10$^4$ cells or more were injected s.c. or i.v. Since a long survival period may help to distinguish antitumor efficacy of Her-2/neu DNA plasmids, 5×10$^4$ cells were chosen as the initial cell number for i.v. or s.c. tumor challenge. Each mouse received three i.m. injections of 100 µg plasmid DNA according to a preset immunization schedule (FIG. 1b) and one and a half weeks after the third injection of plasmid DNA, each mouse was challenged i.v. or s.c. with 5×10$^4$ Her2-CT26 cells.

In the above subcutaneous tumor model study, all of the animals injected with pTV2 developed palpable tumors (FIG. 5, A). On the other hand, tumors were completely suppressed in all groups of mice each injected with pNeu$_{TM}$, pNeu$_{ECD}$, pNeu$_{TM\text{-}gDs}$, or pNeu$_{ECD\text{-}gDs}$ for 60 days following s.c. tumor injection. In a metastasis model, all group of mice injected with either pNeu$_{TM}$, pNeu$_{ECD}$, pNeu$_{TM\text{-}gDs}$, or pNeu$_{ECD\text{-}gDs}$ survived i.v. tumor challenge (FIG. 5, B). However, four of the seven mice (57%) injected with pTV2 and all mice injected with only PBS did not survive lung metastasis.

Example 5

Comparison of Antitumor Immunity by pNeu$_{ECD}$ and pNeu$_{ECD\text{-}gDs}$

Examples 2 to 4 demonstrated contrasting differences of Her-2/neu-specific antibody titers but comparable CTL responses in mice immunized with different pNeu plasmids. In addition, all groups of mice each immunized with pNeu$_{TM}$, pNeu$_{ECD}$, pNeu$_{TM\text{-}gDs}$, or pNeu$_{ECD\text{-}gDs}$ rejected 5×10$^4$ s.c. tumor challenge. Since the number of tumor cells that were injected s.c. or i.v. into mice was too small to induce tumor in immunized mice, it was very difficult to distinguish antitumor efficacies by the difference in immune response induced by different pNeu constructs. Therefore, the number of tumor cells to be injected was increased by a factor of 100 (5×10$^6$) for s.c. tumor challenge and by a factor of 40 (2×10$^6$) for i.v. tumor challenge relative to that of tumor cells in the first tumor experiment to evaluate the relative importance of Her-2/neu-specific antibody and CTL toward inhibition of Her2-CT26. It was impossible to use a cell number of more than 2×10$^6$ for i.v. tumor challenge because there was the danger of blood vessel blockage by excessive tumor cells injected i.v. Chosen for a comparative purpose was a set of pNeu$_{ECD}$ and pNeu$_{ECD\text{-}gDs}$ that generated the largest difference in Her-2/neu-specific antibody titers among the four different Her-2/neu-expressing plasmids. Each mouse received three i.m. injections of 100 µg plasmid DNA according to the same immunization schedule (FIG. 1, B), and 10 days after the third injection of plasmid DNA, each mouse was challenged s.c. with 5×10$^6$ or i.v. with 2×10$^6$ Her2-CT26.

Figure 6:
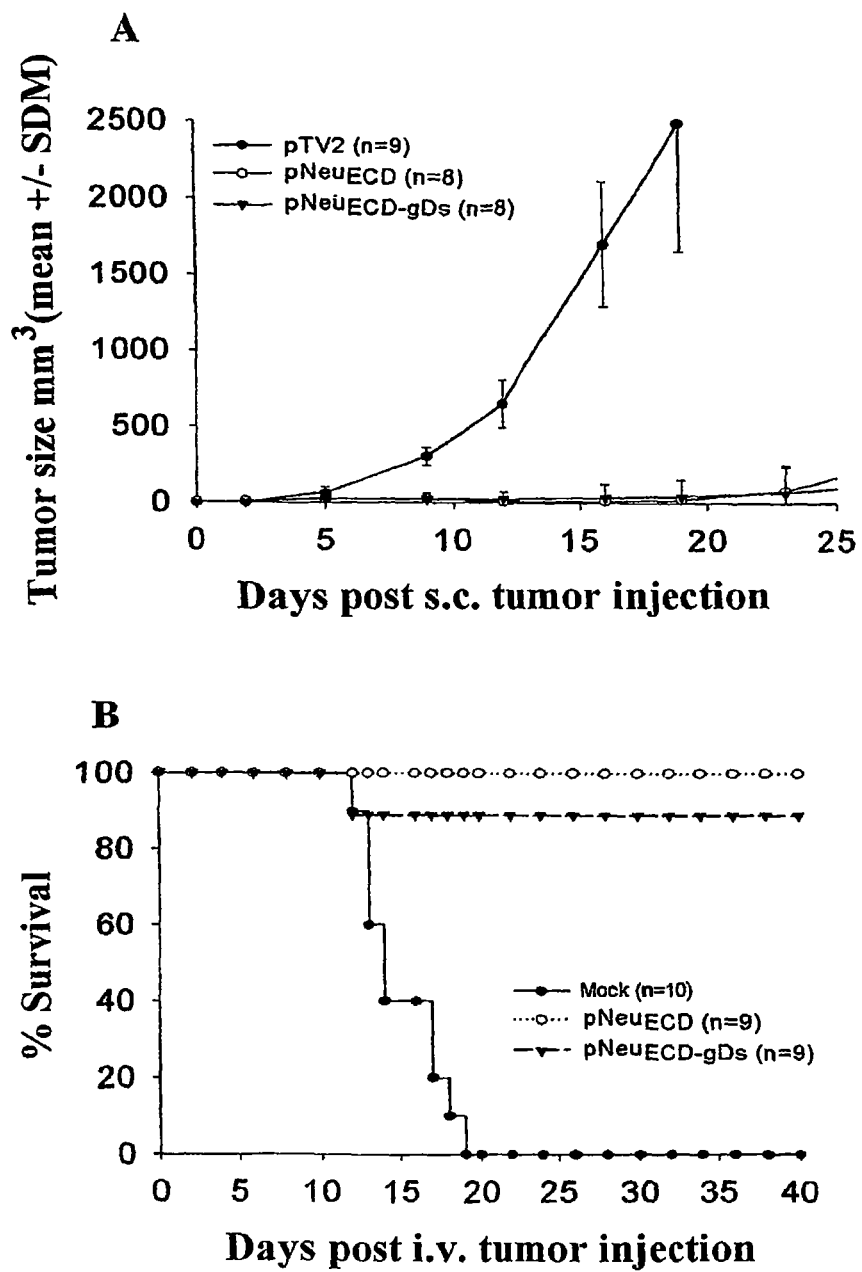
FIG. 6: comparison of preventive antitumor immunity induced by vaccination with pNeu$_{ECD}$ and pNeu$_{ECD-gDs}$;
  A: tumor size in animal model subcutaneously injected of Her2-CT26 cells
  B: survival rate in animal model intravenously injected of Her2-CT26 cells

In the subcutaneous model, all eight animals injected with pTV2 developed tumors and the mean tumor volume reached over 2000 mm$^3$ before day 19 post s.c. tumor challenge (FIG. 6, A). The mean tumor volume of eight mice injected with pNeu$_{ECD}$ was 82.2 mm$^3$ and at day 23 and that of eight mice injected with pNeu$_{ECD\text{-}gDs}$ was 67.9 cm$^3$. While there was significant suppression of tumor growth in mice injected with pNeu$_{ECD}$ (p=2.9900e−8, Student's t test) or pNeu$_{ECD\text{-}gDs}$ (p=2.8400e−8, Student's t test), the difference in the mean tumor volume between the two immunized groups was not statistical significance (P=0.8684, Student's t test). In the metastasis model, lung metastasis was inhibited until day 40 in eight of the eight mice (100%) injected with pNeu$_{ECD}$ and in seven of the eight mice (88%) injected with pNeu$_{ECD\text{-}gDs}$ (FIG. 6, B). All mice vaccinated with pTV2 did not survived lung metastasis. Again, although the survival was significantly prolonged by treatment with pNeu$_{ECD}$ (p<0.0001, Mantel-Haenszel test) or pNeu$_{ECD\text{-}gDs}$ (p=0.0002, Mantel-Haenszel test) compared with pTV2, there was no significant difference between pNeu$_{ECD}$ and pNeu$_{ECD\text{-}gDs}$ (p=0.3173, Mantel-Haenszel test).

Example 6

Efficacy of pNeu Constructs Vaccination in a Therapeutic Model

Preventive model tumor experiments were performed by challenging immunized mice with tumor cells. To compare the antitumor efficacies of pNeu$_{ECD}$ and pNeu$_{ECD\text{-}gDs}$ in a therapeutic model, mice were challenged with tumor cells first, and then received i.m. injections of DNA plasmids. 6-week old naive mice were challenged i.v. with 1×10$^5$ or 5×10$^5$ Her2-CT26 cells, and then were divided into 4 groups. Beginning 1 hour after the tumor injection, each mouse received the first i.m. injection of 100 μg of pNeu$_{ECD}$ or pNeu$_{ECD-gDs}$, followed by four more daily i.m injections with the same DNA plasmid.

Figure 7:
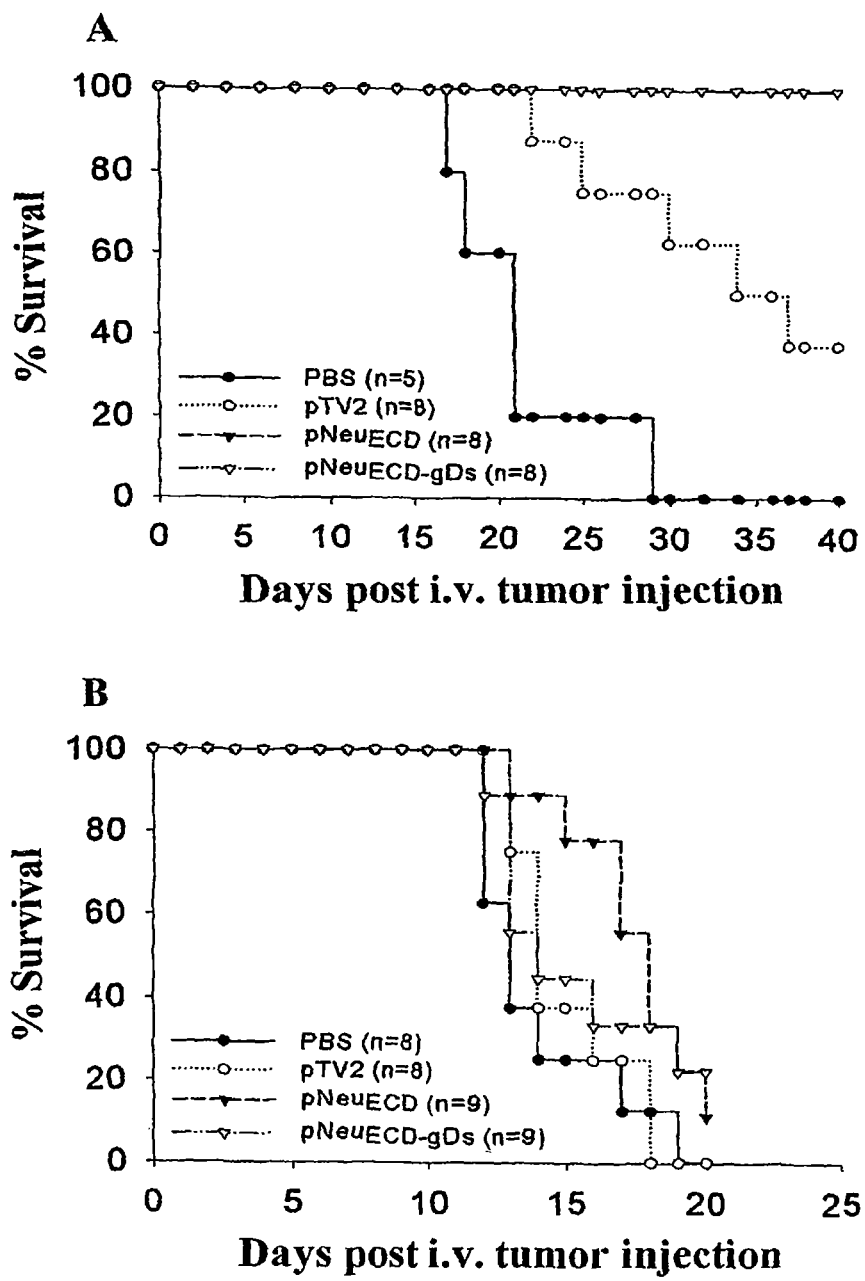
FIG. 7: therapeutic efficacy induced by vaccination with pNeu$_{ECD}$ or pNeu$_{ECD-gDs}$;
  A: 1×10$^5$ Her2-CT26 cells, B: 5×10$^5$ Her2-CT26 cells

The results in FIGS. 5 and 6 show that when 1×10$^5$ tumor cells were injected, all mice treated with pNeu$_{ECD}$ or pNeu$_{ECD-gDs}$ survived lung metastasis for the following 40 days (FIG. 7, A). However, five of the eight mice (63%) injected with pTV2 and all mice (100%) injected with only PBS did not survive lung metastasis. Although pNeu$_{ECD}$ and pNeu$_{ECD-gDs}$ improved the survival rate significantly (p=0.0085, Mantel-Haenszel test) as compared with pTV2, there was no significant difference between pNeu$_{ECD}$ and pNeu$_{ECD-gDs}$.

On the other hand, when the number of tumor cells was increased 5 times (5×10, only the mice injected with pNeu$_{ECD}$ exhibited an increased survival rate which was statistically significantly (p=0.0237, Mantel-Haenszel test) compared with mice injected with pTV2 (FIG. 7, B). However, the mice injected with pNeu$_{ECD-gDs}$ did not show significantly enhanced survival (p=0.4628, Mantel-Haenszel test) as compared with the mice injected with pTV2. Nonetheless, consistently with the preventive model, there was no significant difference in antitumor immunity between pNeu$_{ECD}$ and pNeu$_{ECD-gDs}$ (p=0.4263, Mantel-Haenszel test).

In summary, therapeutic efficacies of Her-2/neu DNA vaccines were evaluated by changing the number of preinjected tumor cells. When mice were treated with a small number of metastatic tumor cells, both pNeu$_{ECD}$ and pNeu$_{ECD-gDs}$ prolonged the survival period significantly and there was no significant difference between their antitumor immunity. However, when a large number of tumor cells were used, only pNeu$_{ECD}$ improved the survival rate.

Example 7

Comparative Analysis of Immune Response Induced by pNeu Constructs and pCK Constructs To enhance the clinical efficacy of vaccine, Her-2/neu DNA plasmid vector was constructed with pCK vector which has stronger promoter activity than pTV2. The KpnI-XbaI fragments of truncated Her-2/neu genes obtained from pNeu$_{ECD}$ and pNeu were each inserted into the KpnI-XbaI site of pCK vector. Thus, pCK expressing the extracellular and transmembrane domains and pCK$_{ECD}$ expressing the extracellular domain of Her-2/neu were prepared.

To evaluate the immunogenicity of pCK and pCK$_{ECD}$, BALB/c mice were vaccinated with pCK$_{TM}$, pCK$_{ECD}$, pNeu$_{ECD}$ and pNeu$_{TM}$ and the sera and spleen were obtained from immunized mice 10 days after the third intramuscular inoculation with each DNA plasmid. SK-BR3 cells were incubated with 400 fold-diluted sera, followed by binding with FITC conjugated goat anti-mouse IgG. Estimation of Her-2/neu specific antibody response was performed by end-point titration using a flow cytometer. The result in FIG. 8 shows that vaccination of mice with pCK$_{TM}$ and pCK$_{ECD}$ induced Her-2/neu-specific IgG antibody responses similar to vaccination with pNeu constructs, wherein uncolored and colored histograms represent control antibody and diluted serum, respectively.

Furthermore, Her-2/neu-specific CTL activity was assayed against Her2-CT26 in a standard $^{51}$Cr-release assay. Vaccination of mice with pCK and pCK$_{ECD}$ also induce strong CTL responses (FIG. 9). CTL responses induced by vaccination of pCK constructs were slightly higher than when vaccinated with pNeu constructs.

Example 8

Antitumor Activity of pCK$_{TM}$ and pCK$_{ECD}$

To determine the antitumor effect of pCK constructs of Her-2/neu, female BALB/c mice were vaccinated intramuscularly three times with 100 μg PBS, pCK, pCK$_{ECD}$ or pCK$_{TM}$ in two-week intervals, respectively. The mice were challenged s.c. or i.v. with 1×10$^6$ Her2-CT26 2 weeks after final vaccination. The three-dimensional size of grown solid tumor induced by s.c. injection of Her2-CT26 was measured with a caliper. The number of live mice was counted everyday and the results were presented as the percentage of live mice per treatment group.

Figure 10:
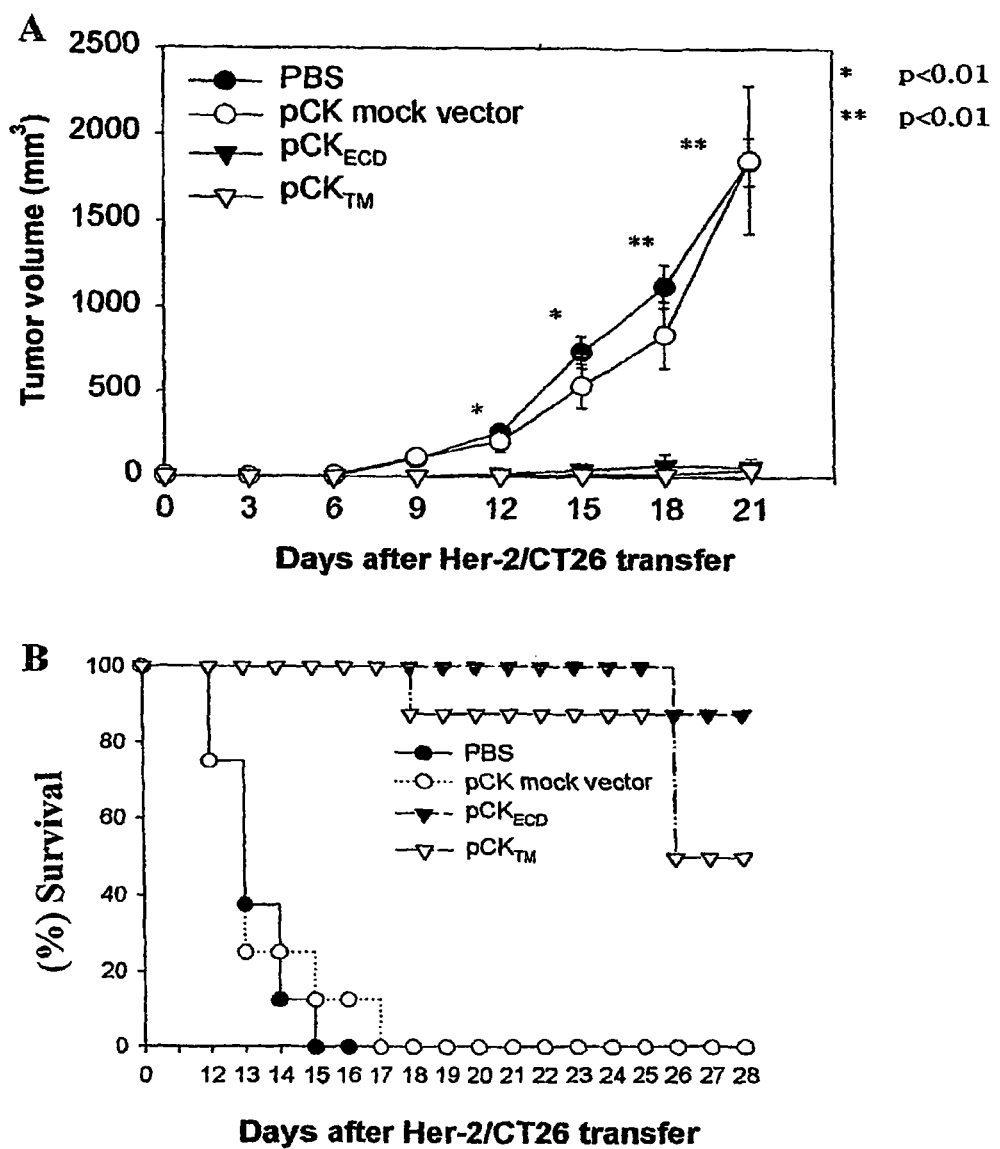
FIG. 10: preventive antitumor immunity induced by vaccination with pCK$_{ECD}$ and pCK$_{TM}$;
  A: tumor size in animal model subcutaneously injected of Her2-CT26 cells
  B: survival rate in animal model intravenously injected of Her2-CT26 cells

Growth of solid tumors induced by s.c. injection of Her2-CT26 was inhibited completely in the mice vaccinated with pCK or pCK$_{ECD}$ (FIG. 10, A). In the lung metastasis model, pCK$_{TM}$ and pCK$_{ECD}$ prolonged the survival period, demonstrating strong suppression of lung metastasis (FIG. 10, B). In summary, protective immunity against Her2-CT26 challenge also could be achieved by vaccination with pCK$_{TM}$ or pCK$_{ECD}$.

Figure 11:
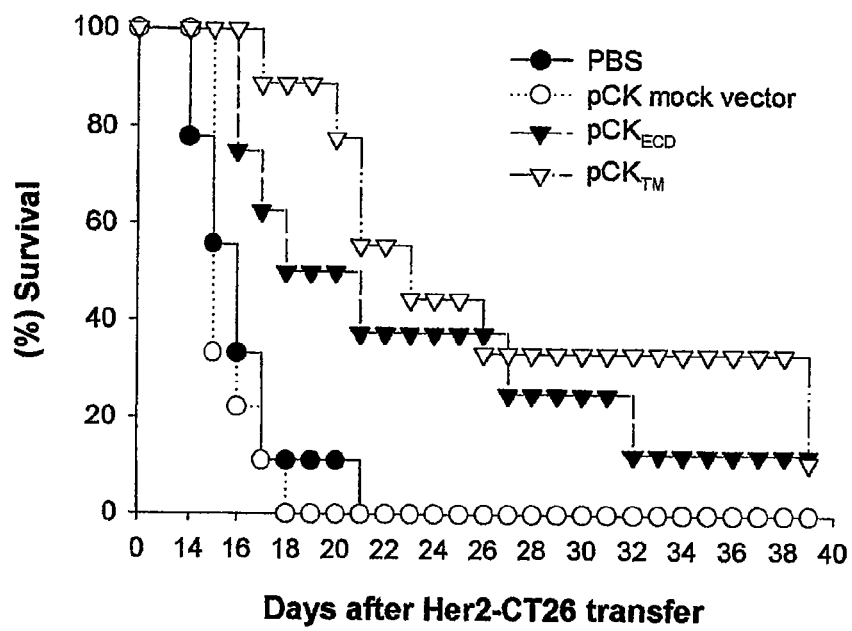
FIG. 11: therapeutic efficacies induced by vaccination with pCK$_{ECD}$ and pCK$_{TM}$.

To test therapeutic effects of pCK$_{TM}$ and pCK$_{ECD}$, mice were vaccinated intramuscularly with 100 μg PBS, pCK, pCK$_{ECD}$ or pCK$_{TM}$, 1 hr after 2×10$^5$ Her2-CT26 i.v. challenge. The number of live mice was counted everyday and the results were presented as the percentage of live mouse per treatment group. Post-vaccination with pCK$_{TM}$ or pCK$_{ECD}$ was effective for the protection against the growth of metastatic colony and appeared to inhibit death by lung metastasis (FIG. 11). Thus, preventive antitumor effects of pNeu constructs were retained in pCK$_{TM}$ and pCK$_{ECD}$. Furthermore, in the therapeutic model to evaluate protective immunity against preinjected tumor cells, pCK$_{TM}$ and pCK$_{ECD}$ prolonged the survival rate significantly. Since therapeutic antitumor activity of pCK was slightly better than that of pCK$_{ECD}$, pCK$_{TM}$ was chosen as a model for Her-2/neu DNA vaccine in combination with cytokine genes.

Example 9

Immune Responses and Antitumor Activities Induced by Coinjection of pCK$_{TM}$ and Various Cytokine Plasmids To use cytokine genes as a molecular adjuvant in the Her-2/neu DNA vaccination, six cytokine gene-contained pCK vectors, pCK-GMCSF, pCK-IL12, pCK-IL15, pCK-IL18, pCK-Eta1 and pCK-Flt3L, were prepared as follows. GM-CSF and Flt3L, which promote the proliferation and activation of antigen presenting cells, are expected to improve the delivery efficiency into professional antigen presenting cells like dendritic cells and to increase immune responses. IL-12, IL-15, IL-18 and Eta-1 are representative T$_H$1 skewing cytokines and expected to induce cell-mediated immune responses important to cancer immunity.

Eta-1 (SEQ ID NO: 10), IL-18 (SEQ ID NO: 11), IL-15 (SEQ ID NO: 12) and Flt3L (SEQ ID NO: 13) genes were amplified from mRNA isolated from the spleen of BALB/c mice by RT-PCR (SUPERSCRIPT™ II RT, GIBCO BRL) with specific primers (Eta-1, with EF1 of SEQ ID NO: 14 and ER1 of SEQ ID NO: 15; IL-18, with 18F1 of SEQ ID NO: 16 and 18R1 of SEQ ID NO: 17; IL-15, with 15F1 of SEQ ID NO: 18 and 15R1 of SEQ ID NO: 19; and Flt3L, with FF1 of SEQ ID NO: 20 and FR1 of SEQ ID NO: 21) according to the manufacturer's instructions. Cloned cytokine genes were inserted into pCK to generate pCK-Eta1, pCK-IL18, pCK-IL15 and pCK-Flt3L. pCK-GMCSF and pCK-IL12 were constructed by inserting the EcoRI-XbaI and XhoI fragments of pTV2-GMCSF (Cho, J. H. et al., *Vaccine* 17: 1136-1144, 1999) and pTV2-IL12 (Ha, S. J. et al., *Nat. Biotechnol.* 20: 381-386, 2002), into pCK vector, respectively.

To analyze the effects of cytokine gene adjutants in the antibody production and CTL response, mice were intramuscularly injected with $pCK_{TM}$ and each of the pCK-cytokines (FIG. 12a). 3 weeks after the final vaccination, antibody titration was performed by a flow cytometry to determine Her-2/neu-specific antibody production and $^{51}$Cr-release assay, to measure CTL responses.

TABLE 2

| | | Her-2/neu specific IgG titer | | | | | |
|---|---|---|---|---|---|---|---|
| Mice | PCK | $pCK_{TM}$ | +IL-12 | +IL-15 | +IL-18 | +Eta-1 | +Flt3L | +GM-CSF |
| 1 | <50 | 3200 | 6400 | 6400 | 6400 | 3200 | 800 | 3200 |
| 2 | <50 | 3200 | 3200 | 3200 | 6400 | 3200 | 3200 | 6400 |
| 3 | <50 | 6400 | 6400 | 1600 | 6400 | 6400 | 800 | 6400 |
| 4 | <50 | 3200 | 400 | 1600 | 12800 | 6400 | 1600 | 1600 |

Figure 12B:
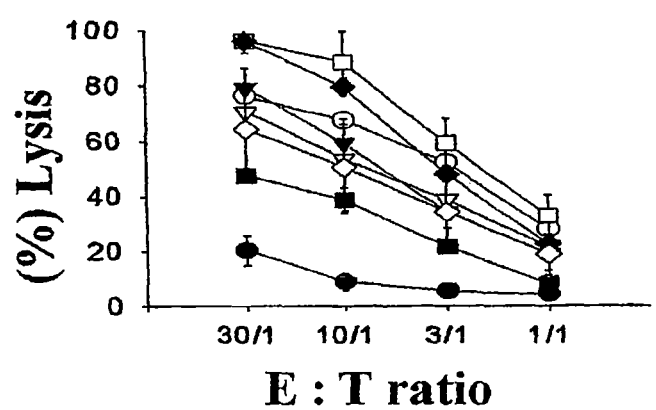
Figure 12B:
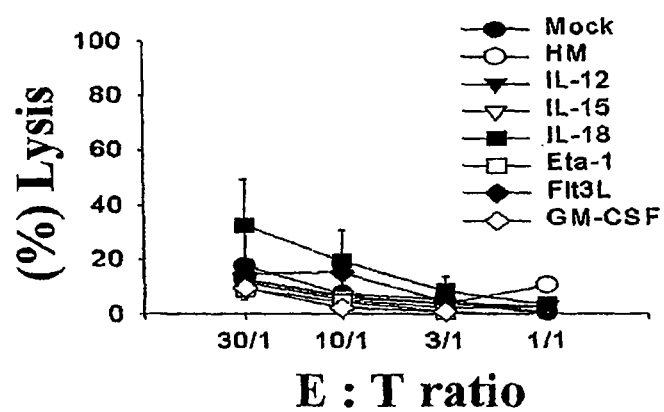

As shown in Table 2, Her-2/neu-specific antibodies were sufficiently produced by vaccination of $pCK_{TM}$ with or without cytokines but no significant difference was found for the groups coinjected with cytokine gene plasmids (FIG. 12b).

TABLE 3

| | Effector:Target ratio | | |
|---|---|---|---|
| | 3:1 | 10:1 | 30:1 |
| pCK | 5.5 ± 0.69 | 8.8 ± 3.16 | 20.3 ± 5.43 |
| $pCK_{TM}$ | 52.6 ± 6.03 | 67.6 ± 0.56 | 76.4 ± 1.21 |
| $pCK_{TM}$ + pCK-IL12 | 34.6 ± 5.67 | 59.3 ± 8.82 | 79.3 ± 6.99 |
| $pCK_{TM}$ + pCK-IL15 | 39.0 ± 0.76 | 53.6 ± 1.08 | 70.7 ± 6.30 |
| $pCK_{TM}$ + pCK-IL18 | 21.8 ± 1.44 | 38.8 ± 1.53 | 47.7 ± 2.55 |
| $pCK_{TM}$ + pCK-Eta1 | 59.5 ± 9.01 | 88.7 ± 11.07 | 96.2 ± 4.52 |
| $pCK_{TM}$ + pCK-Flt3L | 48.4 ± 2.99 | 79.6 ± 3.22 | 95.9 ± 2.38 |
| $pCK_{TM}$ + pCK-GMCSF | 34.6 ± 12.96 | 50.6 ± 15.56 | 64.3 ± 13.8 |

Table 3 shows a summary of the CTL responses observed in FIG. 12b. As shown in Table 3, the percentage of target lysis increased slightly by vaccination of $pCK_{TM}$ with pCK-Eta1 or pCK-Flt3L but decreased slightly by vaccination of $pCK_{TM}$ with pCK-IL18 or pCK-GMCSF. Nonspecific lysis using CT26 as target cell was not found in all mice.

Example 10

Antitumor Activity Induced by Coinjection of $pCK_{TM}$ and Cytokine Plasmids

Figure 13A:
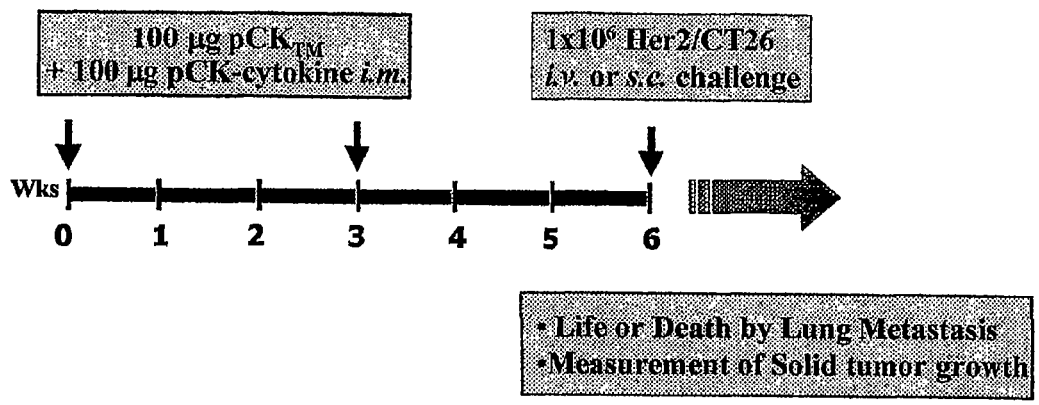
FIGS. 13a to 13d: preventive antitumor effect induced by co-injection with pCK$_{TM}$ and cytokine plasmids, wherein 13a shows vaccination schedule; 13b, tumor size in subcutaneous injection model of Her2-CT26 cells (a parenthesis means the percentage of mouse having no tumor growth per treatment group); 13c and 13d, survival rate in intravenous injection model of Her2-CT26 cells (a parenthesis means the percentage of live mouse per treatment group)
Figure 14A:
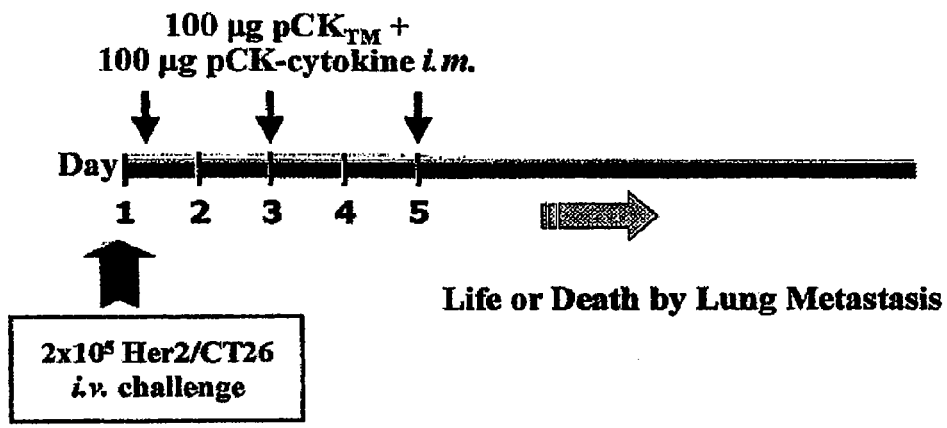
FIGS. 14a to 14c: therapeutic efficacies induced by co-injection with pCK$_{TM}$ and pCK-cytokine plasmids, wherein 14a shows vaccination schedule; 14b and 14c, survival rate in intravenous injection model vaccination with pCK$_{TM}$-cytokine plasmids of Her2-CT26 cells (a parenthesis means the percentage of live mouse per treatment group)

To determine antitumor activity induced by coinjection of $pCK_{TM}$ and a cytokine plasmid, preventive and therapeutic experiments were performed using BALB/c mice. As shown in FIG. 13a and FIG. 14a, BALB/c mice were challenged with Her2-CT26 cells after and before vaccination with $pCK_{TM}$ and each of the cytokine plasmids. BALB/c mice were co-injected i.m. with 100 μg $pCK_{TM}$ and 100 μg each of the pCK-cytokine plasmids. The mice were challenged i.v. or s.c. with 1×10$^6$ Her2-CT26 at week 3 after the $2^{nd}$ vaccination. Tumor growth was measured with a caliper twice a week and the volume was calculated for each mouse.

Figure 13B:
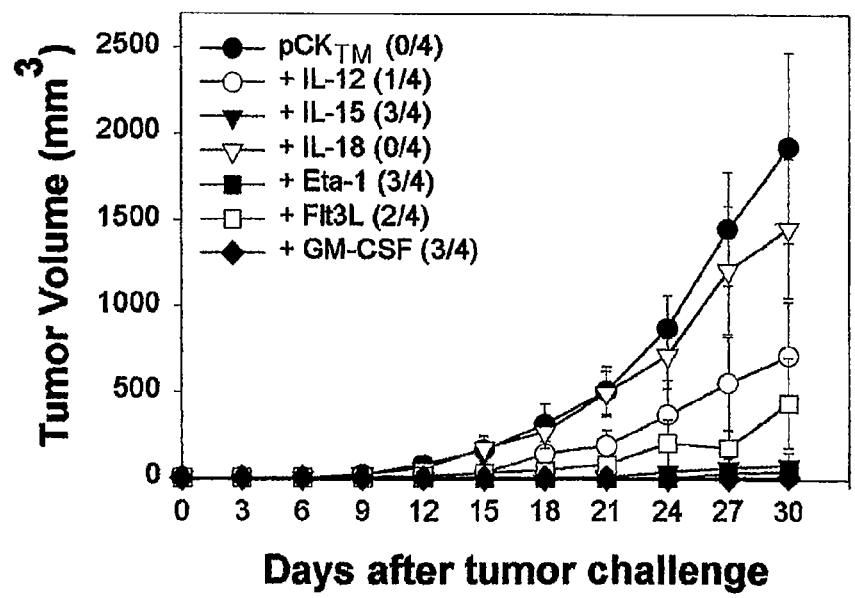
Figure 13C:
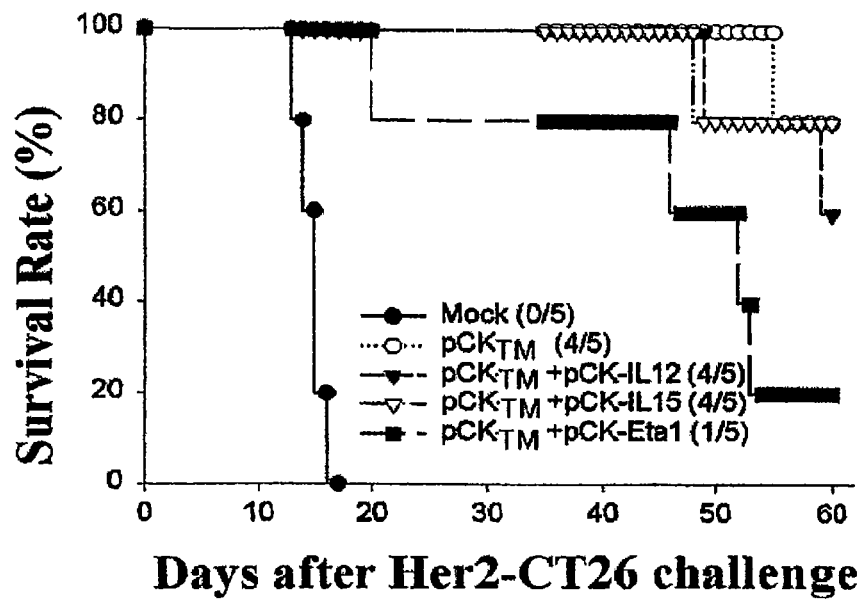
Figure 13D:
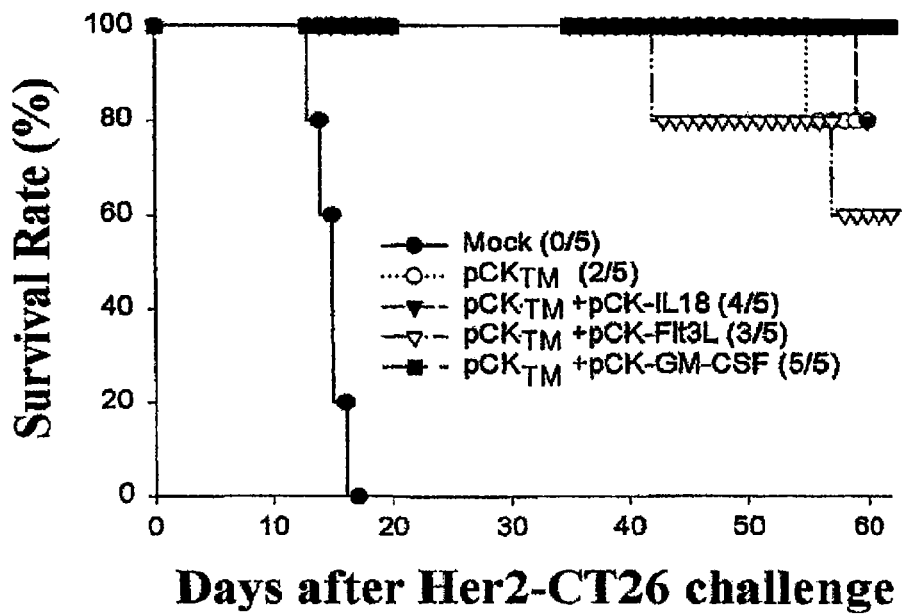

The growth of subcutaneous tumor was inhibited by covaccination with $pCK_{TM}$ and a cytokine plasmid, especially pCK-GMCSF, pCK-Eta1 and pCK-IL15 (FIG. 13b). Metastases of intravenously challenged Her2-CT26 were inhibited by vaccination with $pCK_{TM}$ and pCK-GMCSF (FIGS. 13c and 13d).

Figure 14B:
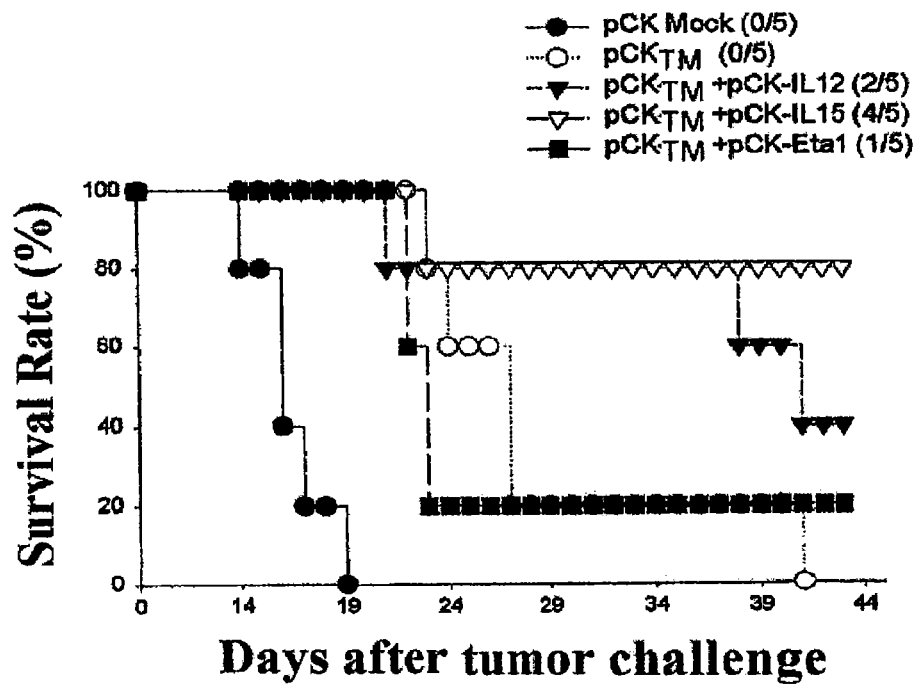
Figure 14C:
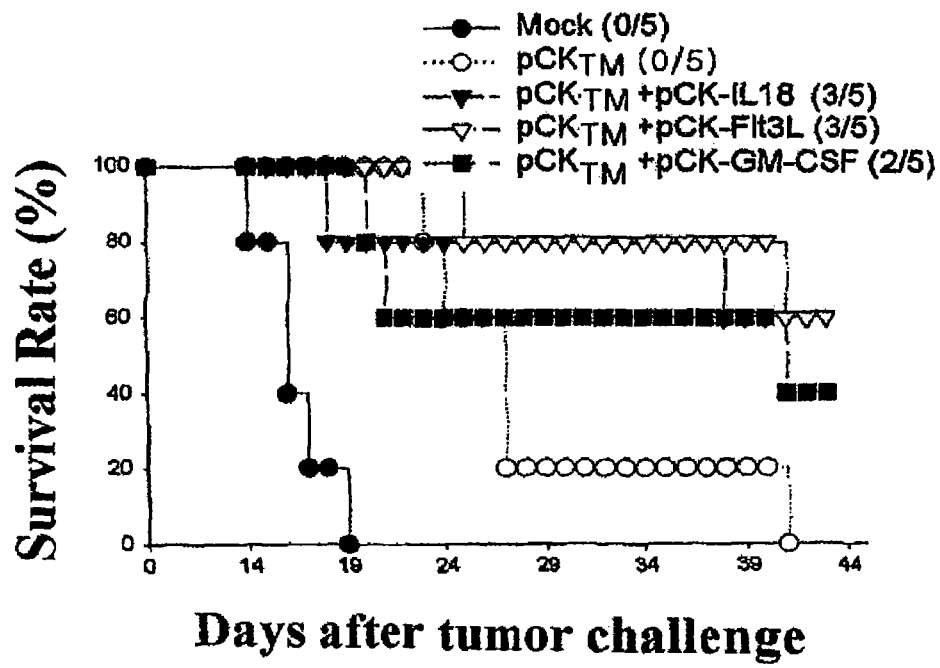

Mice were vaccinated intramuscularly with 100 μg $pCK_{TM}$ and each of the pCK-cytokine plasmids after 2×10$^5$ Her2-CT26 i.v. challenge. The number of live mice was counted everyday and the results were presented as the percentage of live mouse per treatment group. Co-vaccination with $pCK_{TM}$ and pCK-cytokine plasmids except pCK-Eta1 improved the survival rate more than when vaccinated only with $pCK_{TM}$ (FIGS. 14b and 14c).

Therefore, the preventive antitumor activity of $pCK_{TM}$ was promoted by co-injection of a particular cytokine plasmid such as pCK-GMCSF both in tumor growth model and metastasis model.

Example 11

Construction of Bicistronic Plasmids Expressing Her-2/neu and Cytokine

Figure 15A:
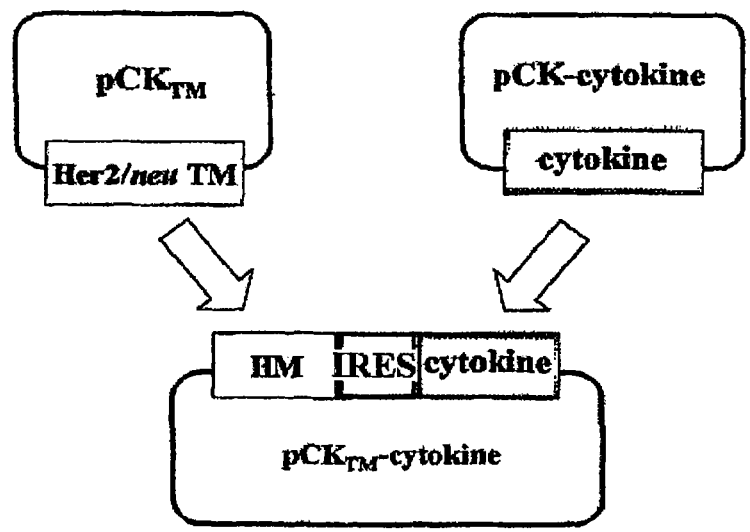
FIGS. 15a to 15d: preventive antitumor effect induced by pCK$_{TM}$-cytokine plasmids, wherein 15a shows schematic procedure of constructing bicistronic plasmids; 15b, vaccination schedule; 15c, tumor size in subcutaneous injection model of Her2-CT26 cells (a parenthesis means the percentage of mouse having no tumor growth per treatment group); 15d, survival rate in intravenous injection model of Her2-CT26 cells (a parenthesis means the percentage of live mouse per treatment group)

To enhance the antitumor activity of Her-2/neu DNA vaccination, constructed were bicistronic plasmids, $pCK_{TM}$-GMCSF, $pCK_{TM}$-Flt3L, $pCK_{TM}$-Eta1, $pCK_{TM}$-IL12, $pCK_{TM}$-IL15, $pCK_{TM}$-IL18 and $pCK_{TM}$-IL23, in which the Her-2/neu protein and each of the cytokines had been translated independently. The internal ribosomal entry site (IRES) of encephalomyocarditis virus (EMCV) between the Her-2/neu gene and cytokine gene enabled the simultaneous expression of Her-2/neu protein and cytokine (FIG. 15a).

To generate bicistronic plasmids co-expressing Her-2/neu and cytokine proteins, GM-CSF, Flt3L, IL-15, IL-18 and Eta-1 genes were amplified by PCR using specific primers as described in Example 9, which were inserted downstream of IRES of EMCV of $pCK_{TM}$-IRES. IRES of EMCV having the nucleotide sequence of SEQ ID NO: 22 was derived from pCK-IL12. For IL-12 and IL-23 (Belladonna, M. L., et al., *J. Immunol.* 168: 5448-5454, 2002), IRES was amplified by PCR using pCK-IL12 as a template and IRES-F1 of SEQ ID NO: 23 and IRES-R1 of SEQ ID NO: 24 as a primer pair, and the amplified product was inserted into the NotI-XhoI site of $pCK_{TM}$ to obtain $pCK_{TM}$-IRES.

Example 12

Figure 15B:
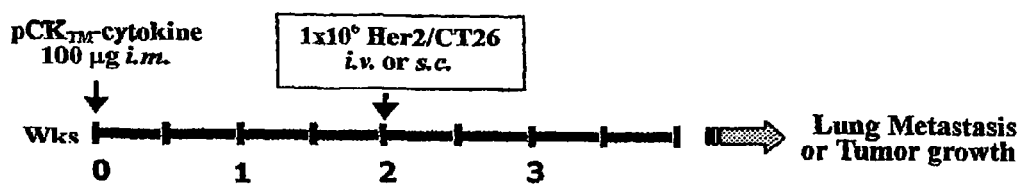

Antitumor Effects Induced by Bicistronic Plasmids Expressing Her-2/neu and Cytokine To evaluate preventive antitumor activities of $pCK_{TM}$-cytokine plasmids, mice were vaccinated with each of the seven $pCK_{TM}$-cytokine plasmids ($pCK_{TM}$-GMCSF, $pCK_{TM}$-Flt3L, pCK$_{TM}$-Eta1, pCK$_{TM}$-IL12, pCK$_{TM}$-IL15, pCK$_{TM}$-IL18 and pCK$_{TM}$-IL23) according to the vaccination schedule shown in FIG. 15b.

Figure 15C:
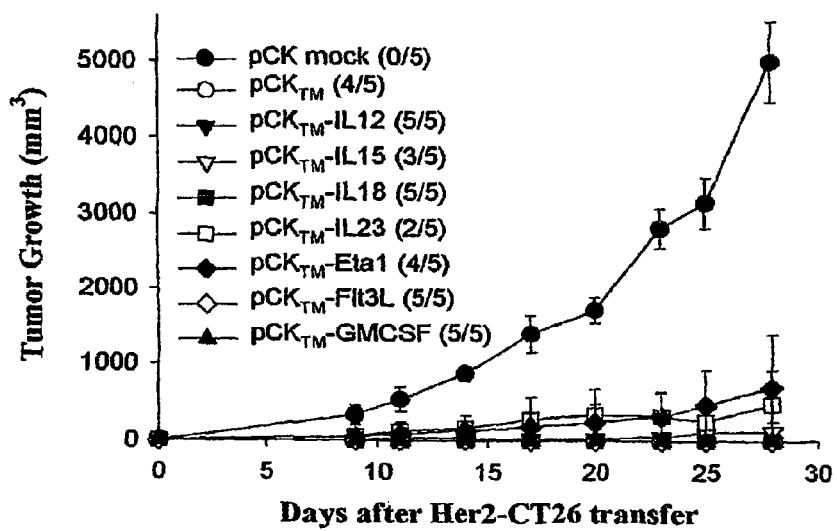
Figure 15D:
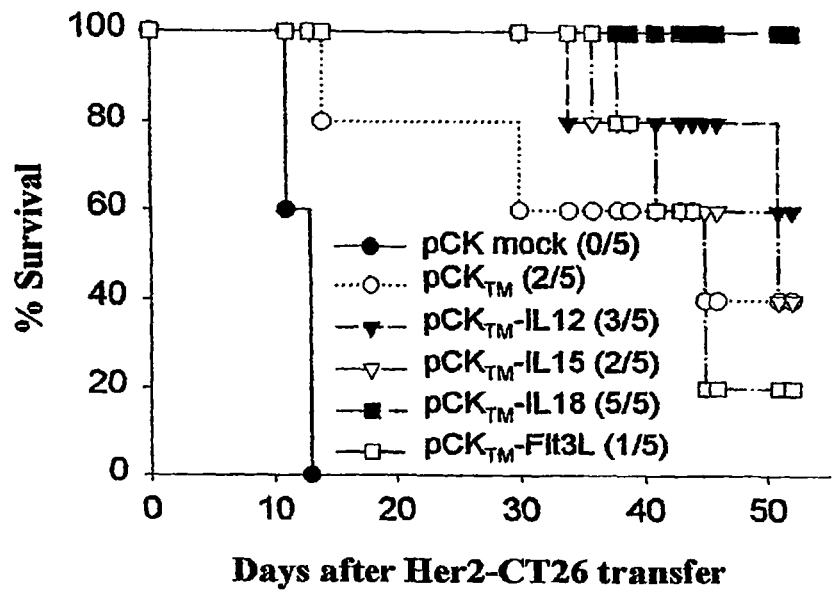
Figure 15D:
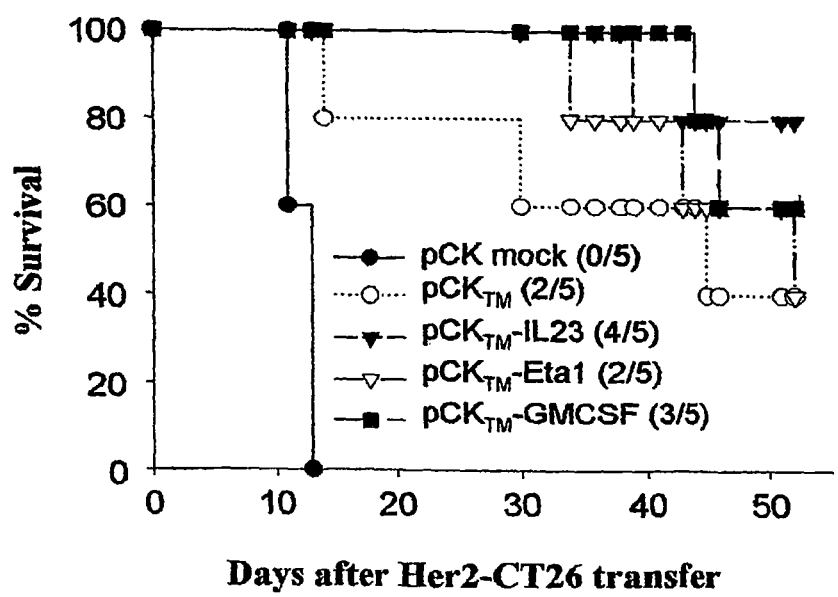
Figure 16:
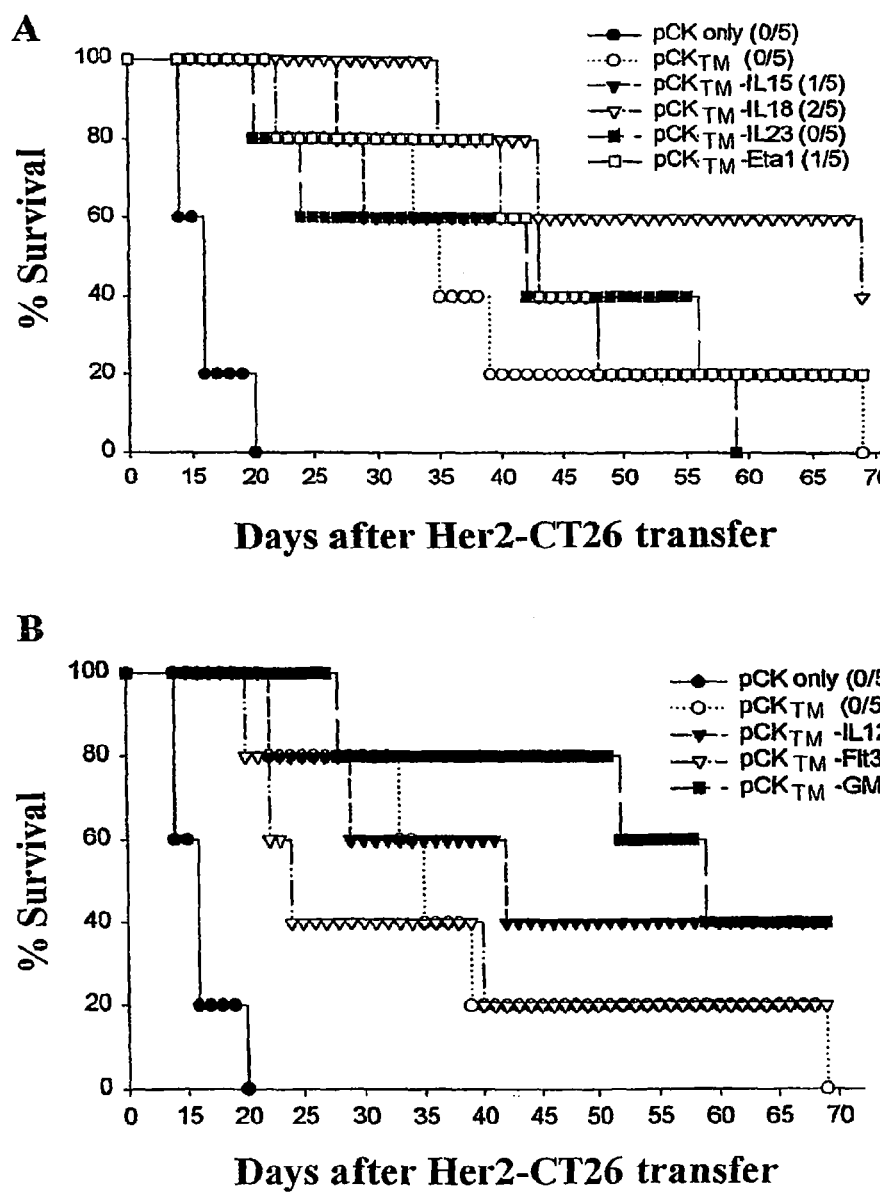
FIGS. 16A and B: therapeutic efficacies induced by pCK$_{TM}$-cytokine plasmids.

Intramuscular inoculation with pCK$_{TM}$-cytokine constructs inhibited more thoroughly the growth of tumor implanted subcutaneously than when only pCK was injected (FIG. 15c). Especially, pCK$_{TM}$-IL18, pCK$_{TM}$-GMCSF, pCK$_{TM}$-IL12 and pCK$_{TM}$-Flt3L exhibited outstanding effects in the inhibition of tumor growth. In the tumor metastasis model, pCK$_{TM}$-IL18 completely protected mice from lung metastasis (FIG. 15d). Anti-metastatic effects of other bicistronic constructs were similar to the case of pCK$_{TM}$. Protection against metastasis of preinjected Her2-CT26 was assayed in the treatment model according to the schedule shown in FIG. 14a. Vaccination with pCK$_{TM}$-GMCSF and pCK$_{TM}$-IL18 prolonged the survival rate (FIG. 16, A and B). Collectively, pCK$_{TM}$-GMCSF and pCK$_{TM}$-IL18 appeared to markedly increase tumor suppression effects in the preventive and therapeutic model.

While the embodiments of the subject invention have been described and illustrated, it is obvious that various changes and modifications can be made therein without departing from the spirit of the present invention which should be limited only by the scope of the appended claims.

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. Chang-Yuil Kang
PanGenomics, Inc., Innovation Center,
Institute of Molecular Biology and Genetics,
Seoul National University, Sillimdong,
Kwanakgu, Seoul 151-057, Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: pNeuTM | Accession number given by the INTERNATIONAL DEPOSITARY AUTHORITY: KCCM-10393 |

| II. SCIENTIFIC DESCRIPTION AND/OR PROPOSED TAXONOMIC DESIGNATION |
|---|
| The microorganism identified under I above was accompanied by: <br> ☐ a scientific description <br> ☐ a proposed taxonomic designation <br> (Mark with a cross where applicable) |

| III. RECEIPT AND ACCEPTANCE |
|---|
| This International Depositary Authority accepts the microorganism identified under I above, which was received by it on Jun. 26. 2002. (date of the original deposit)¹ |

| IV. INTERNATIONAL DEPOSITARY AUTHORITY | |
|---|---|
| Name: Korean Culture Center of Microorganisms <br><br> Address: 361-221, Yurim B/D <br> Hongje-1-dong, <br> Seodaemun-gu <br> SEOUL 120-091 <br> Republic of Korea | Signature(s) of person(s) having the power to represent the International Depositary Authority or of authorized official(s): <br><br> Date: Jul. 3. 2002 |

1 Where Rule 6.4(d) applies, such date is the date on which the status of international depositary authority was acquired : where a deposit made outside the Budapest Treaty after the acquisition of the status of international depositary authority is converted into a deposit under the Budapest Treaty, such date is the date on which the microorganism was received by the international depositary authority.

Form BP/4                                                                                           Sole page BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. Chang-Yuil Kang
PanGenomics, Inc., Innovation Center,
Institute of Molecular Biology and Genetics,
Seoul National University, Sillimdong,
Kwanakgu, Seoul 151-057, Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: pNeuECD | Accession number given by the INTERNATIONAL DEPOSITARY AUTHORITY: KCCM-10394 |

| II. SCIENTIFIC DESCRIPTION AND/OR PROPOSED TAXONOMIC DESIGNATION |
|---|
| The microorganism identified under I above was accompanied by: <br> ☐ a scientific description <br> ☐ a proposed taxonomic designation <br> (Mark with a cross where applicable) |

| III. RECEIPT AND ACCEPTANCE |
|---|
| This International Depositary Authority accepts the microorganism identified under I above, which was received by it on Jun. 26. 2002. (date of the original deposit)[1] |

| IV. INTERNATIONAL DEPOSITARY AUTHORITY | |
|---|---|
| Name : Korean Culture Center of Microorganisms <br><br> Address : 361-221, Yurim B/D <br> Hongje-1-dong, <br> Seodaemun-gu <br> SEOUL 120-091 <br> Republic of Korea | Signature(s) of person(s) having the power to represent the International Depositary Authority or of authorized official(s): <br><br> Date: Jul. 3. 2002 |

[1] Where Rule 6.4(d) applies, such date is the date on which the status of international depositary authority was acquired : where a deposit made outside the Budapest Treaty after the acquisition of the status of international depositary authority is converted into a deposit under the Budapest Treaty, such date is the date on which the microorganism was received by the international depositary authority.

Form BP/4                                                                                           Sole page BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. Chang-Yuil Kang
    PanGenomics, Inc., Innovation Center,
    Institute of Molecular Biology and Genetics,
    Seoul National University, Sillimdong,
    Kwanakgu, Seoul 151-057, Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: pCK-ECD | Accession number given by the INTERNATIONAL DEPOSITARY AUTHORITY: KCCM-10395 |

| II. SCIENTIFIC DESCRIPTION AND/OR PROPOSED TAXONOMIC DESIGNATION |
|---|
| The microorganism identified under I above was accompanied by: <br> ☐ a scientific description <br> ☐ a proposed taxonomic designation <br> (Mark with a cross where applicable) |

| III. RECEIPT AND ACCEPTANCE |
|---|
| This International Depositary Authority accepts the microorganism identified under I above, which was received by it on Jun. 26, 2002. (date of the original deposit)[1] |

| IV. INTERNATIONAL DEPOSITARY AUTHORITY | |
|---|---|
| Name : Korean Culture Center of Microorganisms <br><br> Address : 361-221, Yurim B/D <br> Hongje-1-dong, <br> Seodaemun-gu <br> SEOUL 120-091 <br> Republic of Korea | Signature(s) of person(s) having the power to represent the International Depositary Authority or of authorized official(s): <br><br> Date: Jul. 3, 2002 |

[1] Where Rule 6.4(d) applies, such date is the date on which the status of international depositary authority was acquired : where a deposit made outside the Budapest Treaty after the acquisition of the status of international depositary authority is converted into a deposit under the Budapest Treaty, such date is the date on which the microorganism was received by the international depositary authority.

Form BP/4      Sole page

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

To. Chang-Yuil Kang
   PanGenomics, Inc., Innovation Center,
   Institute of Molecular Biology and Genetics,
   Seoul National University, Sillimdong,
   Kwanakgu, Seoul 151-057, Korea RECEIPT IN THE CASE OF AN ORIGINAL
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: pCK-TM | Accession number given by the INTERNATIONAL DEPOSITARY AUTHORITY: KCCM-10396 |

| II. SCIENTIFIC DESCRIPTION AND/OR PROPOSED TAXONOMIC DESIGNATION |
|---|
| The microorganism identified under I above was accompanied by: <br> ☐ a scientific description <br> ☐ a proposed taxonomic designation <br> (Mark with a cross where applicable) |

| III. RECEIPT AND ACCEPTANCE |
|---|
| This International Depositary Authority accepts the microorganism identified under I above, which was received by it on Jun. 26. 2002. (date of the original deposit)[1] |

| IV. INTERNATIONAL DEPOSITARY AUTHORITY | |
|---|---|
| Name: Korean Culture Center of Microorganisms <br><br> Address: 361-221, Yurim B/D <br> Hongje-1-dong, <br> Seodaemun-gu <br> SEOUL 120-091 <br> Republic of Korea | Signature(s) of person(s) having the power to represent the International Depositary Authority or of authorized official(s): <br><br> Date: Jul. 3. 200 |

[1] Where Rule 6.4(d) applies, such date is the date on which the status of international depositary authority was acquired : where a deposit made outside the Budapest Treaty after the acquisition of the status of international depositary authority is converted into a deposit under the Budapest Treaty, such date is the date on which the microorganism was received by the international depositary authority.

Form BP/4                                                             Sole page

What is claimed is:

1. A bicistronic plasmid construct comprising a polynucleotide encoding a signal peptide, a C-terminally truncated human Her-2/neu protein comprising the entire extracellular domain (ECD) and the transmembrane domain (TM) of Her-2/neu, but not the intracellular domain (ICD) of Her-2/neu, and granulocyte-macrophage colony-stimulating factor (GM-CSF), wherein the polynucleotide further comprises an internal ribosomal entry site (IRES) having the nucleotide sequence of SEQ ID NO: 22 between a nucleotide sequence encoding the truncated human Her-2/neu protein and a nucleotide sequence encoding the GM-CSF.

2. The construct of claim 1, wherein said truncated human Her-2/neu protein is encoded by the nucleotide sequence of SEQ ID NO: 2.

3. The construct of claim 1, wherein said plasmid construct is a pCK plasmid construct.

4. The construct of claim 3, wherein construct is $pCK_{TM-GMCSF}$.

5. A pharmaceutical composition comprising the construct of claim 1 and a pharmaceutically acceptable carrier.

6. A method for treating a Her-2/neu-over-expressing human cancer comprising intramuscularly administering an effective amount of a bicistronic plasmid construct comprising a polynucleotide encoding a signal peptide, a C-terminally truncated human Her-2/neu protein comprising the entire extracellular domain (ECD) and the transmembrane domain (TM) of Her-2/neu, but not the intracellular domain (ICD) of Her-2/neu, and GM-CSF to a mammal in need of treatment of a Her-2/neu-over-expressing human cancer, wherein the polynucleotide further comprises an internal ribosomal entry site (IRES) having the nucleotide sequence of SEQ ID NO: 22 between a nucleotide sequence encoding the truncated human Her-2/neu protein and a nucleotide sequence encoding the GM-CSF, thereby treating said Her-2/neu-over-expressing human cancer.

7. The method of claim 6, wherein said truncated human Her-2/neu protein is encoded by the nucleotide sequence of SEQ ID NO: 2.

8. The method of claim 6, wherein said construct is a pCK plasmid construct.

9. The method of claim 8, wherein construct is $pCK_{TM-GMCSF}$.

10. The method of claim 6, wherein said cancer is breast cancer or ovary cancer.

11. The method of claim 10, wherein said cancer is breast cancer.

12. The method of claim 6, wherein said cancer comprises a solid tumor.

13. A method of preventing or reducing Her-2/neu over-expressing tumor growth in a mammal, comprising intramuscularly administering an effective amount of a bicistronic plasmid construct comprising a polynucleotide encoding a signal peptide, a C-terminally truncated human Her-2/neu protein comprising the entire extracellular domain (ECD) and the transmembrane domain (TM) of Her-2/neu, but not the intracellular domain (ICD) of Her-2/neu, and GM-CSF, wherein the nucleotide comprises an internal ribosomal entry site (IRES) having the nucleotide sequence of SEQ ID NO: 22 between a nucleotide sequence encoding the truncated human Her-2/neu protein and a nucleotide sequence encoding the GM-CSF to a mammal in need of preventing or reducing Her-2/neu over-expressing cancer; thereby preventing or reducing Her-2/neu over-expressing tumor growth in said mammal.

14. The method of claim 13, wherein said truncated human Her-2/neu protein is encoded by the nucleotide sequence of SEQ ID NO: 2.

15. The method of claim 13, wherein said cancer is breast cancer or ovary cancer.

16. The method of claim 13, wherein said tumor is a solid tumor.

* * * * *

SEQUENCE LISTING

<160> NUMBER OF SEQ ID NOS: 24

<210> SEQ ID NO 1
<211> LENGTH: 4530
<212> TYPE: DNA
<213> ORGANISM: Homo sapiens

<400> SEQUENCE: 1

| | | | | | | |
|---|---|---|---|---|---|---|
| aattctcgag | ctcgtcgacc | ggtcgacgag | ctcgagggtc | gacgagctcg | agggcgcgcg | 60 |
| cccggccccc | acccctcgca | gcaccccgcg | ccccgcgccc | tcccagccgg | gtccagccgg | 120 |
| agccatgggg | ccggagccgc | agtgagcacc | atggagctgg | cggccttgtg | ccgctggggg | 180 |
| ctcctcctcg | ccctcttgcc | ccccggagcc | gcgagcaccc | aagtgtgcac | cggcacagac | 240 |
| atgaagctgc | ggctccctgc | cagtcccgag | acccacctgg | acatgctccg | ccacctctac | 300 |
| cagggctgcc | aggtggtgca | gggaaacctg | gaactcacct | acctgcccac | caatgccagc | 360 |
| ctgtccttcc | tgcaggatat | ccaggaggtg | cagggctacg | tgctcatcgc | tcacaaccaa | 420 |
| gtgaggcagg | tcccactgca | gaggctgcgg | attgtgcgag | gcacccagct | ctttgaggac | 480 |
| aactatgccc | tggccgtgct | agacaatgga | gacccgctga | caataccac | ccctgtcaca | 540 |
| ggggcctccc | caggaggcct | gcgggagctg | cagcttcgaa | gcctcacaga | gatcttgaaa | 600 |
| ggaggggtct | tgatccagcg | gaacccccag | ctctgctacc | aggacacgat | tttgtggaag | 660 |
| gacatcttcc | acaagaacaa | ccagctggct | ctcacactga | tagacaccaa | ccgctctcgg | 720 |
| gcctgccacc | cctgttctcc | gatgtgtaag | ggctcccgct | gctggggaga | gagttctgag | 780 |
| gattgtcaga | gcctgacgcg | cactgtctgt | gccggtggct | gtgcccgctg | caaggggcca | 840 |
| ctgcccactg | actgctgcca | tgagcagtgt | gctgccggct | gcacgggccc | caagcactct | 900 |
| gactgcctgg | cctgcctcca | cttcaaccac | agtggcatct | gtgagctgca | ctgcccagcc | 960 |
| ctggtcacct | acaacacaga | cacgtttgag | tccatgccca | atcccgaggg | ccggtataca | 1020 |
| ttcggcgcca | gctgtgtgac | tgcctgtccc | tacaactacc | tttctacgga | cgtgggatcc | 1080 |
| tgcacctcg | tctgccccct | gcacaaccaa | gaggtgacag | cagaggatgg | aacacagcgg | 1140 |
| tgtgagaagt | gcagcaagcc | ctgtgcccga | gtgtgctatg | gtctgggcat | ggagcacttg | 1200 |
| cgagaggtga | gggcagttac | cagtgccaat | atccaggagt | ttgctggctg | caagaagatc | 1260 |
| tttgggagcc | tggcatttct | gccggagagc | tttgatgggg | acccagcctc | caacactgcc | 1320 |
| ccgctccagc | cagagcagct | ccaagtgttt | gagactctgg | aagagatcac | aggttaccta | 1380 |
| tacatctcag | catggccgga | cagcctgcct | gacctcagcg | tcttccagaa | cctgcaagta | 1440 |
| atccggggac | gaattctgca | caatggcgcc | tactcgctga | ccctgcaagg | gctgggcatc | 1500 |
| agctggctgg | ggctgcgctc | actgagggaa | ctgggcagtg | gactggccct | catccaccat | 1560 |
| aacacccacc | tctgcttcgt | gcacacggtg | ccctgggacc | agctctttcg | gaacccgcac | 1620 |
| caagctctgc | tccacactgc | caaccggcca | gaggacgagt | gtgtgggcga | gggcctggcc | 1680 |
| tgccaccagc | tgtgcgcccg | agggcactgc | tgggtccag | gcccacccca | gtgtgtcaac | 1740 |
| tgcagccagt | tccttcgggg | ccaggagtgc | gtggaggaat | gccgagtact | gcagggctc | 1800 |
| cccagggagt | atgtgaatgc | caggcactgt | ttgccgtgcc | accctgagtg | tcagccccag | 1860 |
| aatggctcag | tgacctgttt | tggaccggag | gctgaccagt | gtgtggcctg | tgcccactat | 1920 |
| aaggaccctc | ccttctgcgt | ggccgcctgc | cccagcggtg | tgaaacctga | cctctcctac | 1980 |
| atgcccatct | ggaagtttcc | agatgaggag | ggcgcatgcc | agccttgccc | catcaactgc | 2040 |

```
acccactcct gtgtggacct ggatgacaag ggctgccccg ccgagcagag agccagccct   2100
ctgacgtcca tcgtctctgc ggtggttggc attctgctgg tcgtggtctt gggggtggtc   2160
tttgggatcc tcatcaagcg acggcagcag aagatccgga agtacacgat gcggagactg   2220
ctgcaggaaa cggagctggt ggagccgctg acacctagcg gagcgatgcc caaccaggcg   2280
cagatgcgga tcctgaaaga cacggagctg aggaaggtga aggtgcttgg atctggcgct   2340
tttggcacag tctacaaggg catctggatc cctgatgggg agaatgtgaa aattccagtg   2400
gccatcaaag tgttgaggga aaacacatcc cccaaagcca acaaagaaat cttagacgaa   2460
gcatacgtga tggctggtgt gggctcccca tatgtctccc gccttctggg catctgcctg   2520
acatccacgg tgcagctggt gacacagctt atgcccctatg gctgcctctt agaccatgtc   2580
cgggaaaacc gcggacgcct gggctcccag gacctgctga actggtgtat gcagattgcc   2640
aaggggatga gctacctgga ggatgtgcgg ctcgtacaca gggacttggc cgctcggaac   2700
gtgctggtca agagtcccaa ccatgtcaaa attacagact cgggctggc tcggctgctg   2760
gacattgacg agacagagta ccatgcagat gggggcaagg tgcccatcaa gtggatggcg   2820
ctggagtcca ttctccgccg gcggttcacc caccagagtg atgtgtggag ttatggtgtg   2880
actgtgtggg agctgatgac ttttggggcc aaaccttacg atgggatccc agcccgggag   2940
atccctgacc tgctggaaaa gggggagcgg ctgccccagc cccccatctg caccattgat   3000
gtctacatga tcatggtcaa atgttggatg attgactctg aatgtcggcc aagattccgg   3060
gagttggtgt ctgaattctc ccgcatggcc agggaccccc agcgctttgt ggtcatccag   3120
aatgaggact tgggcccagc cagtcccttg gacagcacct tctaccgctc actgctggag   3180
gacgatgaca tgggggacct ggtggatgct gaggagtatc tggtaccccca gcagggcttc   3240
ttctgtccag accctgcccc gggcgctggg ggcatggtcc accacaggca ccgcagctca   3300
tctaccagga gtggcggtgg ggacctgaca ctagggctgg agccctctga agaggaggcc   3360
cccaggtctc cactggcacc ctccgaaggg gctggctccg atgtatttga tggtgacctg   3420
ggaatggggg cagccaaggg gctgcaaagc ctccccacac atgacccag ccctctacag   3480
cggtacagtg aggaccccac agtacccctg ccctctgaga ctgatggcta cgttgccccc   3540
ctgacctgca gcccccagcc tgaatatgtg aaccagccag atgttcggcc ccagcccct   3600
tcgccccgag agggccctct gcctgctgcc cgacctgctg gtgccactct ggaaagggcc   3660
aagactctct ccccagggaa gaatgggggtc gtcaaagacg ttttgccctt ggggggtgcc   3720
gtggagaacc ccgagtactt gacacccag ggaggagctg cccctcagcc ccaccctcct   3780
cctgccttca gcccagcctt cgacaacctc tattactggg accaggaccc accagagcgg   3840
ggggctccac ccagcacctt caaagggaca cctacggcag agaacccaga gtacctgggt   3900
ctggacgtgc cagtgtgaac cagaaggcca agtccgcaga agccctgatg tgtcctcagg   3960
gagcagggaa ggcctgactt ctgctggcat caagaggtgg gagggccctc cgaccacttc   4020
caggggaacc tgccatgcca ggaacctgtc ctaaggaacc ttccttcctg cttgagttcc   4080
cagatggctg gaaggggtcc agcctcgttg gaagaggaac agcactgggg agtctttgtg   4140
gattctgagg ccctgcccaa tgagactcta gggtccagtg gatgccacag cccagcttgg   4200
cccttttcctt ccagatcctg ggtactgaaa gccttaggga agctggcctg agaggggaag   4260
cggccctaag ggagtgtcta agaacaaaag cgacccattc agagactgtc cctgaaacct   4320
agtactgccc cccatgagga aggaacagca atggtgtcag tatccaggct ttgtacagag   4380
tgcttttctg tttagttttt actttttttg ttttgttttt ttaaagacga aataaagacc   4440
```

```
cagggagaa tgggtgttgt atggggaggc aagtgtgggg ggtccttctc cacacccact    4500
ttgtccattt gcaaatatat tttggaaaac                                   4530

<210> SEQ ID NO 2
<211> LENGTH: 2052
<212> TYPE: DNA
<213> ORGANISM: Homo sapiens

<400> SEQUENCE: 2
atggagctgg cggccttgtg ccgctggggg ctcctcctcg ccctcttgcc ccccggagcc     60
gcgagcaccc aagtgtgcac cggcacagac atgaagctgc ggctccctgc cagtcccgag    120
acccacctgg acatgctccg ccacctctac cagggctgcc aggtggtgca gggaaacctg    180
gaactcacct acctgcccac caatgccagc ctgtccttcc tgcaggatat ccaggaggtg    240
cagggctacg tgctcatcgc tcacaaccaa gtgaggcagg tcccactgca gaggctgcgg    300
attgtgcgag caccagct ctttgaggac aactatgccc tggccgtgct agacaatgga    360
gacccgctga acaataccac ccctgtcaca ggggcctccc aggaggcct gcgggagctg    420 cagcttcgaa gcctcacaga gatcttgaaa ggaggggtct tgatccagcg gaaccccag    480 ctctgctacc aggacacgat tttgtggaag acatcttcc acaagaacaa ccagctggct    540
ctcacactga tagacaccaa ccgctctcgg gcctgccacc cctgttctcc gatgtgtaag    600
ggctcccgct gctggggaga gagttctgag gattgtcaga gctgacgcg cactgtctgt    660 gccggtggct gtgcccgctg caaggggcca ctgcccactg actgctgcca tgagcagtgt    720
gctgccggct gcacgggccc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcgcgcca gctgtgtgac tgcctgtccc    900
tacaactacc tttctacgga cgtgggatcc tgcaccctcg tctgccccct gcacaaccaa    960
gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcattttct gccggagagc   1140 tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgcaagta atccggggac gaattctgca caatggcgcc   1320
tactcgctga cctgcaagg gctgggcatc agctggctgg gctgcgctc actgagggaa   1380 ctgggcagtg gactggccct catccaccat aacacccacc tctgcttcgt gcacacggtg   1440
ccctgggacc agctctttcg gaacccgcac caagctctgc tccacactgc aaccggcca   1500 gaggacgagt gtgtgggcga gggcctggcc tgccaccagc tgtgcgcccg agggcactgc   1560
tggggtccag gcccacccca gtgtgtcaac tgcagccagt tccttcgggg ccaggagtgc   1620
gtggaggaat gccgagtact gcaggggctc cccaggagt atgtgaatgc aggcactgt   1680 ttgccgtgcc accctgagtg tcagcccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactcct gtgtggacct ggatgacaag   1920
ggctgccccg ccgagcagag agccagccct ctgacgtcca tcgtctctgc ggtggttggc   1980
attctgctgg tcgtggtctt gggggtggtc tttgggatcc tcatcaagcg acggcagcag   2040
```

```
aagatccgga ag                                                              2052

<210> SEQ ID NO 3
<211> LENGTH: 1956
<212> TYPE: DNA
<213> ORGANISM: Homo sapiens

<400> SEQUENCE: 3
atggagctgg cggccttgtg ccgctggggg ctcctcctcg ccctcttgcc ccccggagcc     60
gcgagcaccc aagtgtgcac cggcacagac atgaagctgc ggctccctgc cagtcccgag    120
acccacctgg acatgctccg ccacctctac cagggctgcc aggtggtgca gggaaacctg    180
gaactcacct acctgcccac caatgccagc ctgtccttcc tgcaggatat ccaggaggtg    240
cagggctacg tgctcatcgc tcacaaccaa gtgaggcagg tcccactgca gagggctgcg    300
gattgtgcga gcacccagct cttttgagga actatgccc tggccgtgct agacaatgga    360
gacccgctga caataccac ccctgtcaca ggggcctccc caggaggcct gcggagctg    420
cagcttcgaa gcctcacaga gatcttgaaa ggaggggtct tgatccagcg gaaccccag    480
ctctgctacc aggacacgat tttgtggaag gacatcttcc acaagaacaa ccagctggct    540
ctcacactga tagacaccaa ccgctctcgg gcctgccacc cctgttctcc gatgtgtaag    600
ggctcccgct gctggggaga gagttctgag gattgtcaga gcctgacgcg cactgtctgt    660
gccggtggct gtgcccgctg caaggggcca ctgcccactg actgctgcca tgagcagtgt    720
gctgccggct gcacggggcc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcggcgcca gctgtgtgac tgcctgtccc    900
tacaactacc tttctacgga cgtgggatcc tgcaccctcg tctgcccct gcacaaccaa    960
gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgcaagta atccggggac gaattctgca caatggcgcc   1320
tactcgctga cctgcaagg gctgggcatc agctggctgg ggctgcgctc actgagggaa   1380
ctgggcagtg gactggccct catccaccat aacacccacc tctgcttcgt gcacacggtg   1440
ccctgggacc agctctttcg gaacccgcac aagctctgc tccacactgc caaccggcca   1500
gaggacgagt gtgtgggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc ccaggggagt atgtgaatgc aggcactgt   1680
ttgccgtgcc accctgagtg tcagcccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactcct gtgtggacct ggatgacaag   1920
ggctgcccc cgagcagag agccagccct ctgacg                              1956

<210> SEQ ID NO 4
<211> LENGTH: 27
<212> TYPE: DNA
```

<213> ORGANISM: Artificial Sequence
<220> FEATURE:
<223> OTHER INFORMATION: NF6 primer

<400> SEQUENCE: 4
ggtaccatgg agctggcggc cttgtgc                                    27

<210> SEQ ID NO 5
<211> LENGTH: 31
<212> TYPE: DNA
<213> ORGANISM: Artificial Sequence
<220> FEATURE:
<223> OTHER INFORMATION: NSR1 primer

<400> SEQUENCE: 5
gtctagatga ttcacgtcag agggctggct c                               31

<210> SEQ ID NO 6
<211> LENGTH: 23
<212> TYPE: DNA
<213> ORGANISM: Artificial Sequence
<220> FEATURE:
<223> OTHER INFORMATION: NF5 primer

<400> SEQUENCE: 6
gcagtggtac ccaagcttag cac                                        23

<210> SEQ ID NO 7
<211> LENGTH: 27
<212> TYPE: DNA
<213> ORGANISM: Artificial Sequence
<220> FEATURE:
<223> OTHER INFORMATION: NRM2 primer

<400> SEQUENCE: 7
ttctagagca gtctccgcat cgtctac                                    27

<210> SEQ ID NO 8
<211> LENGTH: 28
<212> TYPE: DNA
<213> ORGANISM: Artificial Sequence
<220> FEATURE:
<223> OTHER INFORMATION: NSF2 primer

<400> SEQUENCE: 8
ggcgcgcccc ggcacagaca tgaagctg                                   28

<210> SEQ ID NO 9
<211> LENGTH: 24
<212> TYPE: DNA
<213> ORGANISM: Artificial Sequence
<220> FEATURE:
<223> OTHER INFORMATION: NF3 primer

<400> SEQUENCE: 9
gccgcagcgg ccgccatgga gctg                                       24

<210> SEQ ID NO 10
<211> LENGTH: 1535
<212> TYPE: DNA
<213> ORGANISM: Mus musculus

<400> SEQUENCE: 10
gggggggggg gggggggggg ggggctttcc ttgctcctta tgagaggtgg agaggtagaa    60
aaggcacaca aatattgact cactgaaatt ttctctgaga tgtagaaaga ttccataaat   120

| | | |
|---|---|---|
| tattggtgac ttggtggtga tctagtggtg ccaagagtgt gtttgaacct gacaagacat | 180 | |
| caactgtgcc tcataaaata tgttgcagga ctaactacga ccatgagatt ggcagtgatt | 240 | |
| tgcttttgcc tgtttggcat tgcctcctcc ctcccggtga aagtgactga ttctggcagc | 300 | |
| tcagaggaga agctttacag cctgcaccca gatcctatag ccacatggcc ggtgcctgac | 360 | |
| ccatctcaga agcagaatct ccttgcgcca cagaatgctg tgtcctctga agaaaaggat | 420 | |
| gactttaagc aagaaactct tccaagcaat tccaatgaaa gccatgacca catggacgac | 480 | |
| gatgatgacg atgatgatga cgatggagac catgcagaga gcgaggattc tgtggactcg | 540 | |
| gatgaatctg acgaatctca ccattcggat gagtctgatg agaccgtcac tgctagtaca | 600 | |
| caagcagaca ctttcactcc aatcgtccct acagtcgatg tccccaacgg ccgaggtgat | 660 | |
| agcttggctt atggactgag gtcaaagtct aggagtttcc aggtttctga tgaacagtat | 720 | |
| cctgatgcca cagatgagga cctcacctct cacatgaaga gcggtgagtc taaggagtcc | 780 | |
| ctcgatgtca tccctgttgc ccagcttctg agcatgccct ctgatcagga acaacggaa | 840 | |
| aagggcagcc atgagtcaag tcagctggat gaaccaagtc tggaaacaca cagacttgag | 900 | |
| cattccaaag agagccagga gagtgccgat cagtcggatg tgatcgatag tcaagcaagt | 960 | |
| tccaaagcca gcctggaaca tcagagccac aagtttcaca gccacaagga caagctagtc | 1020 | |
| ctagacccta agagtaagga agatgatagg tatctgaaat tccgaatttc tcatgaatta | 1080 | |
| gagagttcat cttctgaggt caactaaaga agaggcaaaa acacagttcc ttactttgca | 1140 | |
| tttagtaaaa acaagaaaaa gtgttagtga gggttaagca ggaatactaa ctgctcattt | 1200 | |
| ctcagttcag tggatatatg tatgtagaga agagaggta atattttggg ctcttagctt | 1260 | |
| agtctgttgt ttcatgcaaa caccgttgta accaaaagct tctgcacttt gcttctgttg | 1320 | |
| ttcctgtaca agaaatgcaa cggccactgc attttaatga ttgttattct ttcatgaata | 1380 | |
| aaatgtatgt agaaataagt aaatttactg aaacaagcaa gaattaaaag agaaactgta | 1440 | |
| acagtctata tcactatacc cttttagttt tataattagc atatattttg ttgtgattta | 1500 | |
| tttttttttg ttggtgtgaa taaatcttgt taacg | 1535 | |

<210> SEQ ID NO 11
<211> LENGTH: 1535
<212> TYPE: DNA
<213> ORGANISM: Mus musculus

<400> SEQUENCE: 11

| | | |
|---|---|---|
| gggggggggg gggggggggg gggctttcc ttgctcctta tgagaggtgg agaggtagaa | 60 | |
| aaggcacaca aatattgact cactgaaatt ttctctgaga tgtagaaaga ttccataaat | 120 | |
| tattggtgac ttggtggtga tctagtggtg ccaagagtgt gtttgaacct gacaagacat | 180 | |
| caactgtgcc tcataaaata tgttgcagga ctaactacga ccatgagatt ggcagtgatt | 240 | |
| tgcttttgcc tgtttggcat tgcctcctcc ctcccggtga aagtgactga ttctggcagc | 300 | |
| tcagaggaga agctttacag cctgcaccca gatcctatag ccacatggcc ggtgcctgac | 360 | |
| ccatctcaga agcagaatct ccttgcgcca cagaatgctg tgtcctctga agaaaaggat | 420 | |
| gactttaagc aagaaactct tccaagcaat tccaatgaaa gccatgacca catggacgac | 480 | |
| gatgatgacg atgatgatga cgatggagac catgcagaga gcgaggattc tgtggactcg | 540 | |
| gatgaatctg acgaatctca ccattcggat gagtctgatg agaccgtcac tgctagtaca | 600 | |
| caagcagaca ctttcactcc aatcgtccct acagtcgatg tccccaacgg ccgaggtgat | 660 | |
| agcttggctt atggactgag gtcaaagtct aggagtttcc aggtttctga tgaacagtat | 720 | |

| | |
|---|---:|
| cctgatgcca cagatgagga cctcacctct cacatgaaga gcggtgagtc taaggagtcc | 780 |
| ctcgatgtca tccctgttgc ccagcttctg agcatgccct ctgatcagga caacaacgga | 840 |
| aagggcagcc atgagtcaag tcagctggat gaaccaagtc tggaaacaca cagacttgag | 900 |
| cattccaaag agagccagga gagtgccgat cagtcggatg tgatcgatag tcaagcaagt | 960 |
| tccaaagcca gcctggaaca tcagagccac aagtttcaca gccacaagga caagctagtc | 1020 |
| ctagacccta agagtaagga agatgatagg tatctgaaat ccgaatttc tcatgaatta | 1080 |
| gagagttcat cttctgaggt caactaaaga agaggcaaaa acacagttcc ttactttgca | 1140 |
| tttagtaaaa acaagaaaaa gtgttagtga gggttaagca ggaatactaa ctgctcattt | 1200 |
| ctcagttcag tggatatatg tatgtagaga aagagaggta atattttggg ctcttagctt | 1260 |
| agtctgttgt ttcatgcaaa caccgttgta accaaaagct tctgcacttt gcttctgttg | 1320 |
| ttcctgtaca agaaatgcaa cggccactgc atttttaatga ttgttattct ttcatgaata | 1380 |
| aaatgtatgt agaaataagt aaatttactg aaacaagcaa gaattaaaag agaaactgta | 1440 |
| acagtctata tcactatacc cttttagttt tataattagc atatattttg ttgtgattta | 1500 |
| ttttttttg ttggtgtgaa taaatcttgt taacg | 1535 |

<210> SEQ ID NO 12
<211> LENGTH: 1250
<212> TYPE: DNA
<213> ORGANISM: Mus musculus

<400> SEQUENCE: 12

| | |
|---|---:|
| cttctgtcca gccactcttc cccagagttc tcttcttcat cctcccccctt gcagagtagg | 60 |
| gcagcttgca ggtcctcctg caagtctctc ccaattctct cgcccaaaa gacttgcagt | 120 |
| gcatctcctt acgcgctgca gggaccttgc cagggcagga ctgccccgc ccagttgcag | 180 |
| agttggacga agacgggatc ctgctgtgtt tggaaggctg agttccacat ctaacagctc | 240 |
| agagaggtca ggaaagaatc caccttgaca catggccctc tggctcttca aagcactgcc | 300 |
| tcttcatggt ccttgctggt gaggtcctta agaacacaga aacccatgtc agcagataac | 360 |
| cagcctacag gaggccaaga agagttctgg atggatggca gctggaagcc atcgccata | 420 |
| gccagctcat cttcaacatt gaagctctta cctgggcatt aagtaatgaa attttgaaa | 480 |
| ccatatatga ggaatacatc catctcgtgc tacttgtgtt tccttctaaa cagtcacttt | 540 |
| ttaactgagg ctggcattca tgtcttcatt ttgggctgtg tcagtgtagg tctccctaaa | 600 |
| acagaggcca actggataga tgtaagatat gacctggaga aaattgaaag ccttattcaa | 660 |
| tctattcata ttgacaccac tttatacact gacagtgact ttcatcccag ttgcaaagtt | 720 |
| actgcaatga actgctttct cctggaattg caggttattt tacatgagta cagtaacatg | 780 |
| actcttaatg aaacagtaag aaacgtgctc taccttgcaa acagcactct gtcttctaac | 840 |
| aagaatgtag cagaatctgg ctgcaaggaa tgtgaggagc tggaggagaa aaccttcaca | 900 |
| gagttttgc aaagctttat acgcattgtc caaatgttca tcaacacgtc ctgactgcat | 960 |
| gcgagcctct tccgtgtttc tgttattaag gtacctccac ctgctgctca gaggcagcac | 1020 |
| agctccatgc atttgaaatc tgctgggcaa actaagcttc ctaacaagga gataatgagc | 1080 |
| cacttggatc acatgaaatc ttggaaatga agagaggaaa agagctcgtc tcagacttat | 1140 |
| ttttgcttgc ttatttttaa tttattgctt catttgtaca tatttgtaat ataacagaag | 1200 |
| atgtggaata aagttgtatg gatattttat caattgaaat ttaaaaaaaa | 1250 |

<210> SEQ ID NO 13

```
<211> LENGTH: 699
<212> TYPE: DNA
<213> ORGANISM: Mus musculus

<400> SEQUENCE: 13
atgacagtgc tggcgccagc ctggagccca aattcctccc tgttgctgct gttgctgctg      60
ctgagtcctt gcctgcgggg gacacctgac tgttacttca gccacagtcc catctcctcc     120
aacttcaaag tgaagtttag agagttgact gaccacctgc ttaaagatta cccagtcact     180
gtggccgtca atcttcagga cgagaagcac tgcaaggcct tgtggagcct cttcctagcc     240
cagcgctgga tagagcaact gaagactgtg cagggtcta agatgcaaac gcttctggag      300
gacgtcaaca ccgagataca ttttgtcacc tcatgtacct tccagcccct accagaatgt     360
ctgcgattcg tccagaccaa catctcccac ctcctgaagg acacctgcac acagctgctt     420
gctctgaagc cctgtatcgg gaaggcctgc cagaatttct ctcggtgcct ggaggtgcag     480
tgccagccgg actcctccac cctgctgccc ccaaggagtc ccatagccct agaagccacg     540
gagctcccag agcctcggcc caggcagctg ttgctcctgc tgctgctgct gctgcctctc     600
acactggtgc tgctggcagc cgcctggggc cttcgctggc aaagggcaag aaggaggggg     660
gagctccacc ctggggtgcc cctcccctcc catccctag                            699

<210> SEQ ID NO 14
<211> LENGTH: 21
<212> TYPE: DNA
<213> ORGANISM: Artificial Sequence
<220> FEATURE:
<223> OTHER INFORMATION: EF1 primer

<400> SEQUENCE: 14
ctggtaccat gagattggca g                                                21

<210> SEQ ID NO 15
<211> LENGTH: 22
<212> TYPE: DNA
<213> ORGANISM: Artificial Sequence
<220> FEATURE:
<223> OTHER INFORMATION: ER1 primer

<400> SEQUENCE: 15
cctctagatt agttgacctc ag                                               22

<210> SEQ ID NO 16
<211> LENGTH: 25
<212> TYPE: DNA
<213> ORGANISM: Artificial Sequence
<220> FEATURE:
<223> OTHER INFORMATION: 18F1 primer

<400> SEQUENCE: 16
tgaattcatg gctgccatgt cagaa                                            25

<210> SEQ ID NO 17
<211> LENGTH: 23
<212> TYPE: DNA
<213> ORGANISM: Artificial Sequence
<220> FEATURE:
<223> OTHER INFORMATION: 18R1 primer

<400> SEQUENCE: 17
ttctagacta actttgatgt aag                                              23

<210> SEQ ID NO 18
```

<211> LENGTH: 28
<212> TYPE: DNA
<213> ORGANISM: Artificial Sequence
<220> FEATURE:
<223> OTHER INFORMATION: 15F1 primer

<400> SEQUENCE: 18
tgaattcatg aaaattttga aaccatat 28

<210> SEQ ID NO 19
<211> LENGTH: 35
<212> TYPE: DNA
<213> ORGANISM: Artificial Sequence
<220> FEATURE:
<223> OTHER INFORMATION: 15R1 primer

<400> SEQUENCE: 19
ttctagacta aaagctttgc aaaaactctg tgaag 35

<210> SEQ ID NO 20
<211> LENGTH: 24
<212> TYPE: DNA
<213> ORGANISM: Artificial Sequence
<220> FEATURE:
<223> OTHER INFORMATION: FF1 primer

<400> SEQUENCE: 20
tgaattcatg acagtgctgg cgcc 24

<210> SEQ ID NO 21
<211> LENGTH: 24
<212> TYPE: DNA
<213> ORGANISM: Artificial Sequence
<220> FEATURE:
<223> OTHER INFORMATION: FR1 primer

<400> SEQUENCE: 21
ttctagacta ctgcctgggc cgag 24

<210> SEQ ID NO 22
<211> LENGTH: 600
<212> TYPE: DNA
<213> ORGANISM: Encephalomyocarditis virus

<400> SEQUENCE: 22
ggatccgata agcttgatat cgaattccgc cccccccccc cctaacgtta ctggccgaag 60
ccgcttggaa taaggccggt gtgcgtttgt ctatatgtta ttttccacca tattgccgtc 120
ttttggcaat gtgagggccc ggaaacctgg ccctgtcttc ttgacgagca ttcctagggg 180
tctttcccct ctcgccaaag gaatgcaagg tctgttgaat gtcgtgaagg aagcagttcc 240
tctggaagct tcttgaagac aaacaacgtc tgtagcgacc ctttgcaggc agcggaaccc 300
cccacctggc gacaggtgcc tctgcggcca aaagccacgt gtataagata cacctgcaaa 360
ggcggcacaa ccccagtgcc acgttgtgag ttggatagtt gtggaaagag tcaaatggct 420
ctcctcaagc gtattcaaca aggggctgaa ggatgcccaa aaggtacccc attgtatggg 480
atctgatctg gggcctcggg gcacatgctt tacatgtgtt tagtccaggt taaaaaaacg 540
tctaggcccc ccgaaccacg gggacgtggt tttcctttga aaaacacgat aataccatgg 600

<210> SEQ ID NO 23
<211> LENGTH: 31
<212> TYPE: DNA
<213> ORGANISM: Artificial Sequence
<220> FEATURE:

```
<223> OTHER INFORMATION: IRES-F1 primer

<400> SEQUENCE: 23
gcggccgcga taagcttgat atcgaattcc g                              31

<210> SEQ ID NO 24
<211> LENGTH: 27
<212> TYPE: DNA
<213> ORGANISM: Artificial Sequence
<220> FEATURE:
<223> OTHER INFORMATION: IRES-R1 primer

<400> SEQUENCE: 24
ctcgagtatt atcgtgtttt tcaaagg                                   27
```